United States Patent [19]

Finer et al.

[11] Patent Number: 5,686,279
[45] Date of Patent: Nov. 11, 1997

[54] METHOD FOR PRODUCTION OF HIGH TITER VIRUS AND HIGH EFFICIENCY RETROVIRAL MEDIATED TRANSDUCTION OF MAMMALIAN CELLS

[75] Inventors: Mitchell H. Finer, San Carlos; Margo R. Roberts; Thomas J. Dull, both of San Francisco; Krisztina M. Zsebo, Woodside; Lu Qin, Foster City; Deborah A. Farson, Oakland, all of Calif.

[73] Assignee: Cell Genesys, Inc., Foster City, Calif.

[21] Appl. No.: 258,152

[22] Filed: Jun. 10, 1994

Related U.S. Application Data

[63] Continuation-in-part of Ser. No. 76,299, Jun. 11, 1993.
[51] Int. Cl.⁶ .......................... C12N 5/10; C12N 15/64; C12N 15/86
[52] U.S. Cl. ........................ 435/172.3; 435/240.2; 435/320.1; 435/366; 435/325; 435/369
[58] Field of Search ........................ 435/69.1, 172.1, 435/172.3, 240.2, 320.1

[56] References Cited

U.S. PATENT DOCUMENTS

| | | | |
|---|---|---|---|
| 4,405,712 | 9/1983 | Vande Woude et al. | 435/5 |
| 4,650,764 | 3/1987 | Temin et al. | 435/240.2 |
| 4,861,719 | 8/1989 | Miller | 435/236 |
| 5,024,939 | 6/1991 | Gorman | 435/69.1 |

OTHER PUBLICATIONS

Dougherty et al. "New Retrovirus Helper Cells with Almost no Nucleotide Sequence Homology to Retrovirus Vectors," J. Virol., vol. 63, No. 7, pp. 3209–3212, 1989.

Chesebro et al., "Failure of Human Immunodeficiency Virus Entry and Infection in CD4–Positive Human Brain and Skin Cells", Journal of Virology, 64(1):215–221, (1990).

Donahue, et al., "Helper Virus Induced T Cell Lymphoma in Nonhuman Primates after Retroviral mediated Gene Transfer", J. of Experimental Medicine, 176:1125–1135, (1992).

Landau et al., "Pseudotyping with Human T–Cell Leukemia Virus Type I Broadens the Human Immunodeficiency Virus Host Range", Journal of Virology, 65(1):162–169, (1991).

Miller et al., "Construction and Properties of Retrovirus Packaging Cells Based on Gibbon Ape Leukemia Virus", Journal of Virology, (65)5:2220–2224, (1991).

Pedersen et al., "Feline Leukemia Virus Infection as a Potentiating Cofactor for the Primary and Secondary Stages of experimentally Induced Feline Immunodeficiency Virus Infection", Journal of Virology, 64(2):598–606, (1990).

RNA Tumor Viruses, Cold Spring Harbor Laboratory, pp. 26–30, 262–270, 371–380, 393–423, (1984).

van Beusechem et al., "Long–Term Expression of Human Adenosine Deaminase in Rhesus Monkeys Transplanted with Retrovirus–Infected Bone–Marrow Cells", Proc. Natl. Acad. Sci., USA, 89:7640–7644, (1989).

Johnson et al., "A Lethal Myeloproliferative Syndrome in Mice Transplanted with Bone Marrow Cells Infected with a Retrovirus Expressing Granulocyte–Macrophage Colony Stimulating Factor", The EMBO Journal, 8(2):441–448, (1989).

Cepko et al., "Construction and Applications of a Highly Transmissible Murine Retrovirus Shuttle Vector", Cell, 37:1053–1062, (1984).

Amentano et al., "Effect of Internal Viral Sequences on the Utility of Retroviral Vectors", Journal of Virology, 61(5):1647–1650, (1987).

Miller et al., "Generation of Helper–Free Amphotropic Retroviruses That Transduce a Dominant –Acting, Methotrexate–Resistant Dihydrofolate Reductase Gene", Molecular and Cellular Biology, 5(3):431–437, (1985).

Boshart et al., "A Very Strong Enhancer Is Located Upstream of an Immediate Early gene of Human Cytomegalovirus", Cell, 41:521–530, (1985).

Miller et al., "Improved Retroviral Vectors for Gene Transfer and Expression", BioTechniques, 7(9):980–989, (1989).

Apperley et al., Blood, vol. 78, No. 2, "Retroviral Gene Transfer of Human Adenosine Deaminase in Murine Hematopoietic Cells: Effect of Selectable Marker Sequences on Long–Term Expression," Jul. 15, 1991, pp. 310–317.

Armentano et al., Proc. Natl. Acad. Sci. USA, vol. 87, "Expression of human factor IX in rabbit hepatocytes by retrovirus–mediated gene transfer: Potential for gene therapy of hemophilia B, " Aug. 1990, pp. 6141–6145.

Belmont et al., Molecular and Cellular Biology, vol. 8, No. 12, "Expression of Human Adenosine Deaminase in Murine Hematopoietic Cells," Dec. 1988, pp. 5116–5125.

Bosselman et al., Molecular and Cellular Biology, vol. 7, No. 5, "Replication–Defective Chimeric Helper Proviruses and Factors Affecting Generation of Competent Virus: Expression of Moloney murine Leukemia Virus Structural Genes via the Methallothionein Promoter," May 1987, pp. 1797–1806.

Burns et al., Proc. Natl. Acad. Sci. USA, vol. 90, "Vesicular stomatitis virus G glycoprotein pseudotyped retroviral vectors: Concentration to very high titer and efficient gene transfer into mammalian and nonmammalian cells," Sep. 1993, pp. 8033–8037.

(List continued on next page.)

Primary Examiner—David Guzo
Attorney, Agent, or Firm—Karen I. Krupen

[57] ABSTRACT

The invention provides a novel retroviral packaging system, in which retroviral packaging constructs and packagable vector transcripts are produced from high expression plasmids by transfection in human cells. High titers of recombinant retrovirus are produced in infected cells. The methods of the invention include the use of the novel retroviral constructs to transduce primary human cells, including T cells and human hematopoietic stem cells, with foreign genes by cocultivation at high efficiencies. The invention is useful for the rapid production of high viral supernatants, and to transduce with high efficiency cells that are refractory to transduction by conventional means.

18 Claims, 11 Drawing Sheets

OTHER PUBLICATIONS

Cloyd et al., The Journal of Experimental Medicine, vol. 151, "Lumphomagenicity of Recombinant Mink Cell Focus–Inducing Murine Leukemia Viruses," 1980, pp. 542–552.

Cone et al., Proc. Natl. Acad. Sci. USA, vol. 81, "High–efficiency gene transfer into mammalian cells: Generation of helper–free recombinant retrovirus with broad mammalian host range," Oct. 1984, pp. 6349–6353.

Danos et al., Proc. Natl. Acad. Sci. USA, vol. 85, "Safe and efficient generation of recombinant retroviruses with amphotropic and ecotropic host ranges," Sep. 1988, pp. 6460–6464.

Dhawan et al., Science, vol. 254, "Systemic Delivery of Human Growth Hormone by Injection of Genetically Engineered Myoblasts," 6 Dec. 1991, pp. 1509–1511.

Donahue et al., The Journal of Experimental Medicine, vol. 176, "Helper Virus Induced T Cell Lymphoma in Nonhuman Primates after Retroviral Mediated Gene Transfer," Oct. 1992, pp. 1125–1135.

Embretson et al., Virology, vol. 61, No. 9, "Lack of Competition Results in Efficient Packaging of Heterologous Murine Retroviral RNAs and Reticuloendotheliosis Virus Encapsidation–Minus RNAs by the Reticuloendotheliosis Virus Helper Cell Line," Sep. 1987, pp. 2675–2683.

Heinzel et al., Journal of Virology, vol. 62, No. 10, "Use of Simian Virus 40 Replication To Amplify Epstein–Barr Virus Shuttle Vectors in Human Cells," Oct. 1988, pp. 3738–3746.

Landau et al., Journal of Virology, vol. 66, No. 8, "Packaging System for Rapid Production of Murine Leukemia Virus Vectors with Variable Tropism," Aug. 1992, pp. 5110–5113.

Mann et al., Cell, vol. 33, "Construction of a Retrovirus Packaging Mutant and Its Use to Produce Helper–Free Defective Retrovirus," 1983, pp. 153–159.

Markowitz et al., Journal of Virology, vol. 62, No. 4, "A Safe Packaging Line for Gene Transfer: Separating Viral Genes on Two Different Plasmids," Apr. 1988, pp. 1120–1124.

Miller et al., Molecular and Cellular Biology, vol. 6, No. 8, "Redesign of Retrovirus Packaging Cell Lines To Avoid Recombination Leading to Helper Virus Production," Aug. 1986, pp. 2895–2902.

Miller et al., BioTechniques, vol. 7, No. 9, "Improved Retroviral Vectors for Gene Transfer and Expression," 1989, pp. 980–990.

Miller, A. Dusty, Nature, vol. 357, "Human gene therapy comes of age," 11 Jun. 1992, pp. 455–460.

Morecki et al., Cancer Immunol Immunother, vol. 32, "Retrovirus–mediated gene transfer into CD4 + and CD8 + human T cell subsets derived from tumor–infiltrating lymphocytes and peripheral blood mononuclear cells," 1991, pp. 342–352.

Pear et al., Proc. Natl. Acad. Sci. USA, vol. 90, "Production of high–titer helper–free retroviruses by transient transfection," Sep. 1993, pp. 8392–8396.

van Beusecham et al., Proc. Natl. Acad. Sci. USA, vol. 89, "Long–term expression of human adenosine deaminase in rhesus monkeys transplanted with retrovirus–infected bone–marrow cells," Aug. 1992, pp. 7640–7644.

Watanabe et al., Molecular and Cellular Biology, vol. 3, No. 12, "Construction of a Helper Cell Line for Avian Reticuloendotheliosis Virus Cloning Vectors," Dec. 1983, pp. 2241–2249.

Yao et al., Proc. Natl Acad. Sci. USA, vol. 88, "Expression of human factor IX in rat capillary endothelial cells: Toward somatic gene therapy for hemophilia B," Sep. 1991, pp. 8101–8105.

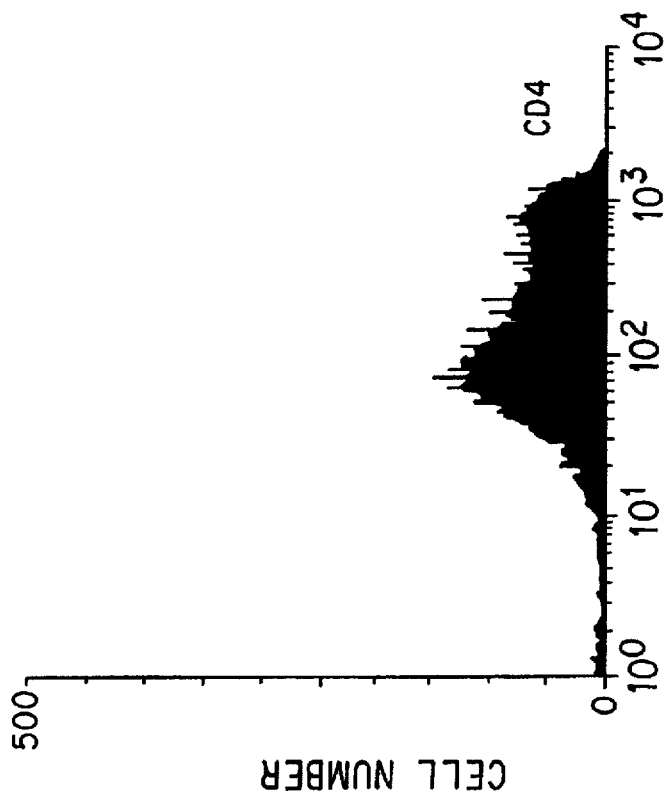
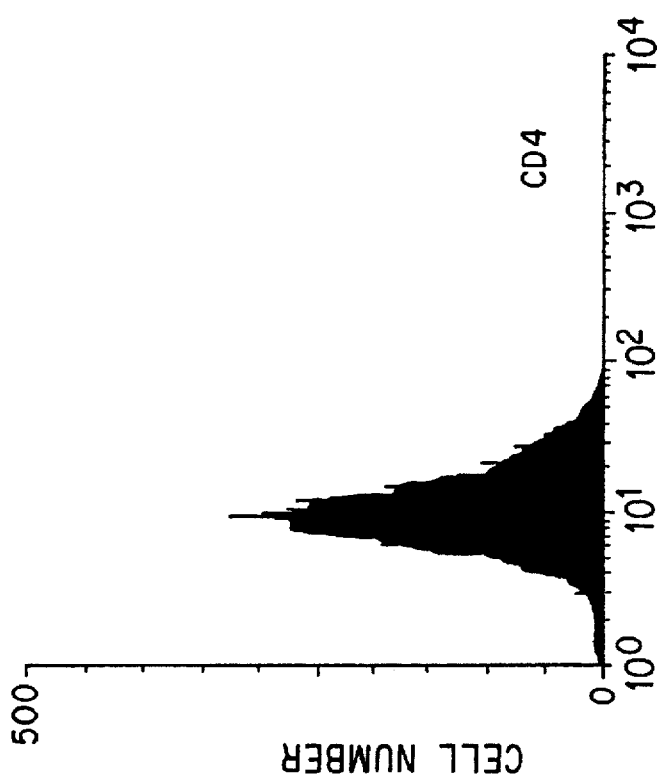

METHOD FOR PRODUCTION OF HIGH TITER VIRUS AND HIGH EFFICIENCY RETROVIRAL MEDIATED TRANSDUCTION OF MAMMALIAN CELLS

CROSS-REFERENCE TO RELATED APPLICATIONS

This application is a continuation-in-part of application Ser. No. 08/076,299, filed Jun. 11, 1993, the disclosure of which is incorporated by reference in its entirety herein.

FIELD OF THE INVENTION

This invention relates to novel retrovirus constructs and their use in transient production of recombinant retrovirus in mammalian cells, and to methods of using such constructs to transduce mammalian cells with high efficiency.

BACKGROUND OF THE INVENTION

Retrovirus vectors have become the primary tool for gene delivery in human gene therapy applications (Miller, *Nature* 357:455–460 (1992)). The ability of retrovirus vectors to deliver an unrearranged, single copy gene into a broad range of rodent, primate and human somatic cells in primary culture makes them well suited for this purpose. Identification and subsequent deletion of the sequences present within retroviral transcripts encoding the packaging signals for avian (E) and murine (ψ) retroviruses, has enabled development of packaging cell lines to supply in trans the proteins necessary for production of infectious virions, but render the packaging cell lines unable to package their own viral genomic mRNA (Watanabe and Temin, *Molec. Cell. Biol.* 3(12):2241–2249 (1983); Mann et al., *Cell* 33:153–159 (1983); and Embretson and Temin, *J. Virol.* 61(9):2675–2683 (1987)). The most important consideration in the construction of retroviral packaging lines has been both the production of high titer vector supernatants free of recombinant replication competent retrovirus, which has been shown to produce T cell lymphomas in rodents (Cloyd et al., *J.Exp.Med.*151,542–552 (1980)) and primates (Donahue et al., *J.Exp.Med.*176,1125–1135 (1992)). Although early murine retroviral packaging lines were highly prone to generation of replication competent retrovirus (RCR) (Cone and Mulligan, *Proc. Nat'l. Acad. Sci. USA* 81:6349–6353 (1984)) or prone to co-package the ψ-genome (Mann et al., supra, 1983; Buttimore and Miller, *Mol. Cell. Biol.* 6(8):2895–2902(1986)), two strategies have evolved for the construction of second generation packaging lines with significantly reduced ability for the generation of RCR. One strategy, embodied by PA317, uses a single genome packaging construct from which the initiation site for second strand synthesis, the 3' LTR, and the ψ site have been deleted (Miller and Buttimore, *Molec. Cell. Biol.* 6(8): 2895–2902 (1986)). These modifications eliminate as much as possible homology between the packaging genome and the viral vector to reduce the ability to form recombinants, and have resulted in production of high titer, helper-free virus with many vector systems (Miller and Rosman, *BioTechniques* 7(9):980–990 (1989)). The second approach has been to divide the packaging functions into two genomes: one that expresses the gag and pol gene products, and the other that expresses the env gene product (Bosselman et al., *Molec. Cell. Biol.* 7(5):1797–1806 (1987); Markowitz et al., *J. Virol.* 62(4):1120–1124 (1988); Danos and Mulligan, *Proc. Nat'l. Acad. Sci. (USA)* 85:6460–6464 (1988)). This approach eliminated the ability for co-packaging and subsequent transfer of the ψ-genome, as well as significantly decreased the frequency of recombination due to the presence of three retroviral genomes in the packaging cell that must undergo recombination to produce RCR. In the event recombinants arise, mutations (Danos and Mulligan, supra) or deletions as (Bosselman et al., supra; and Markowitz et al., supra) within the undesired gene products render recombinants non-functional. In addition, deletion of the 3' LTR on both packaging function constructs further reduces the ability to form functional recombinants. Although early attempts at the generation of two genome packaging lines yielded low titer producer Clones (Bosselman et al., supra) producer lines are new available that yield high titer producer clones (Danos and Mulligan, supra; and Markowitz et al., supra).

Packaging lines currently available yield producer clones of sufficient titer to transduce human cells for gene therapy applications and have led to the initiation of human clinical trials (Miller, supra). However, there are two areas in which these lines are deficient. First, design of the appropriate retroviral vectors for particular applications requires the construction and testing of several vector configurations. For example, Belmont et al., *Molec. and Cell. Biol.* 8(12):5116–5125 (1988), constructed stable producer lines from 16 retroviral vectors in order to identify the vector capable of producing both the highest liter producer and giving optimal expression. Some of the configurations examined included: (1) LTR driven expression vs. an internal promoter; (2) selection of an internal promoter derived from a viral or a cellular gene; and (3) whether a selectable marker was incorporated in the construct. A packaging system that would enable rapid, high-titer virus production without the need to generate stable producer lines would be highly advantageous in that it would save approximately two months required for the identification of high titer producer clones derived from several constructs.

Second, compared to NIH 3T3 cells, the infection efficiency of primary cultures of mammalian somatic cells with a high titer amphotrophic retrovirus producer varies considerably. The transduction efficiency of mouse myoblasts (Dhawan et al., *Science* 254:1509–1512(1991) or rat capillary endothelial cells (Yao et. al., *Proc. Natl. Acad. Sci. USA* 88:8101–8105 (1991)) was shown to be approximately equal to that of NIH 3T3 cells, whereas the transduction efficiency of canine hepatocytes (Armentano et. al., *Proc. Natl. Acad. Sci. USA* 87:6141–6145 (1990)) was only 25% of that found in NIH 3T3 cells. Primary human tumor-infiltrating lymphocytes ("TILs"), human CD4+ and CD8+ T cells isolated from peripheral blood lymphocytes, and primate long-term reconstituting hematopoietic stem cells, represent an extreme example of low transduction efficiency compared to NIH 3T3 cells. Purified human CD4+ and CD8+ T Cells have been reported on one occasion to be infected to levels of 6%–9% with supernatants from stable producer clones (Morecki et al., *Cancer Immunol. Immunother.* 32:342–352 (1991)), and primate or human long-term reconstituting hematopoietic stem cells have only been infected to ≦1% with a producer of titer of $10^6$ per ml on NIH 3T3 cells (van Beusechem et al., *Proc. Natl. Acad. Sci. USA* 89:7640–7644 (1992); and Donahue et al.,supra). If the retrovirus vector contains the $neo^R$ gene, populations that are highly enriched for transduced cells can be obtained by selection in G418. However, selectable marker expression has been shown to have deleterious effects on long-term gene expression in vivo in hematopoietic stem cells (Apperly et.al. *Blood* 78:310–317(1991)).

An approach that yields significantly increased transduction of mammalian cells in primary culture would be highly advantageous, and this need is currently unmet.

SUMMARY OF THE INVENTION

Accordingly, the present invention provides novel plasmid based expression vectors that direct the synthesis of both packagable retroviral vector transcripts and retroviral gene products required for rapid production of high titer recombinant retrovirus in human cells by transient transfection, thereby eliminating the need to generate stable producer lines. In addition, the invention provides a method for highly efficient transduction of mammalian cells that have previously been described as difficult to transduce with retroviral constructs. The invention also describes the construction of cell lines in which the plasmid-based expression vectors of the invention that direct the synthesis of retroviral gene products required in trans for virus production have been stably integrated into the genome of the producing cells. These stably transfected lines can be used to generate stable cell lines that continuously produce recombinant retrovirus at high titer.

The retroviral constructs are packaging plasmids consisting of at least one retroviral helper DNA sequence derived from a replication-incompetent retroviral genome encoding in trans all virion proteins required to package a replication incompetent retroviral vector, and for producing virion proteins capable of packaging the replication-incompetent retroviral vector at high titer, without the production of replication-competent helper virus. The retroviral DNA sequence lacks the region encoding the native enhancer and/or promoter of the viral 5' LTR of the virus, and lacks both the psi function sequence responsible for packaging helper genome and the 3' LTR, but encodes the SV40 polyadenylation site and a foreign enhancer and/or promoter which directs efficient transcription in a cell type where virus production is desired. The retrovirus is a leukemia virus such as a Moloney Murine Leukemia Virus (MMLV), the Human Immunodeficiency Virus (HIV), or the Gibbon Ape Leukemia virus (GALV). The foreign enhancer and promoter may be the human cytomegalovirus (HCMV) immediate early (IE) enhancer and promoter, the enhancer and promoter (U3 region) of the Moloney Murine Sarcoma Virus (MMSV), the U3 region of Rous Sarcoma Virus (RSV), the U3 region of Spleen Focus Forming Virus (SFFV), or the HCMV IE enhancer joined to the native Moloney Murine Leukemia Virus (MMLV) promoter. The retroviral packaging plasmid may consist of two retroviral helper DNA sequences encoded by plasmid based expression vectors, for example where a first helper sequence contains a cDNA encoding the gag and pol proteins of ecotropic MMLV and a second helper sequence contains a cDNA encoding the env protein. The Env gene, which determines the host range, may be derived from the genes encoding xenotrophic, amphotrophic, ecotrophic, polytropic (mink focus forming) or 10A1 murine leukemia virus env proteins, or the Gibbon Ape Leukemia Virus (GALV env protein, the Human Immunodeficiency Virus env (gp160) protein, the Vesicular Stomatitus Virus (VSV) G protein, the Human T cell leukemia (HTLV) type I and II env gene products, chimeric envelope gene derived from combinations of one or more of the aforementioned env genes or chimeric envelope genes encoding the cytoplasmic and transmembrane of the aforementioned env gene products and a monoclonal antibody directed against a specific surface molecule on a desired target cell.

Specific embodiments of the retroviral packaging plasmids of the invention are: pIK6.1MMSVampac, pIK6.1MCVampac, pIK6.1gagpolATG and pIK6.1amenvATG.

The invention includes retroviral vectors that contain a modified 5' LTR, which enables efficient transcription of packagable vector transcripts in the desired cell type. In addition, the invention includes retroviral constructs encoding foreign genes.

In a method of the invention, the packaging plasmids and retroviral vectors are transiently cotransfected into a first population of mammalian cells that are capable of producing virus, such as human embryonic kidney cells, for example 293 cells (ATCC No. CRL1573, ATCC, Rockville, Md.) to produce high titer recombinant retrovirus-containing supernatants. In another method of the invention this transiently transfected first population of cells is then cocultivated with mammalian target cells, for example human lymphocytes, to transduce the target cells with the foreign gene at high efficiencies. The invention further includes target cells expressing a foreign gene produced by the method of the invention. The foreign gene may be a chimeric T cell receptor such as a CD4/zeta or single-antibody chain/zeta T cell receptor.

DETAILED DESCRIPTION OF THE INVENTION

Figure 1:
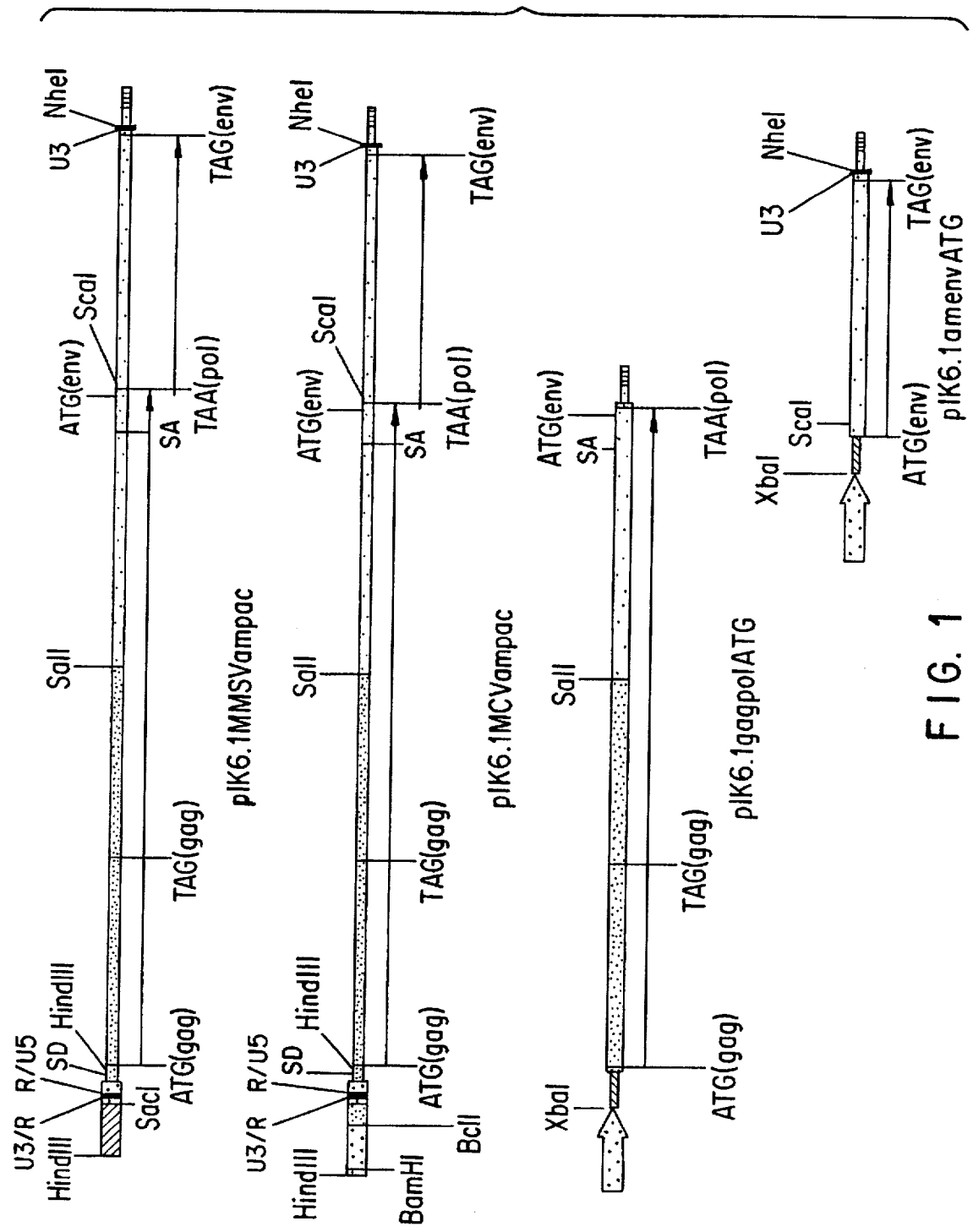
FIG. 1 is a diagrammatic representation of the retroviral packaging plasmids of the invention used to produce the proteins necessary to package retroviral vector transcripts: pIK6.1MMSVampac, pIK6.1MCVampac, pIK6.1gagpolATG, and pIK6.1envATG.

In order that the invention herein described may be more fully understood, the following description is set forth.

The present invention provides novel optimized transient expression plasmids (designated "KAT") for production of retroviral virions in which high steady state levels of retroviral packaging functions and packagable vector transcripts are produced following introduction of KAT plasmids into mammalian cells capable of efficient transient transfection and expression, in the absence of plasmid replication of viral vector and packaging function plasmids. The absence of plasmid replication enables production of high titer virions while minimizing the potential for production of replication competent retrovirus by recombination. Use of the KAT system yields 10-30 fold higher viral titers compared to cotransfection of packaging functions and vector plasmids into COS cells, as described by Landau and Litman, *J. Virol.* 66(8):5110-5113 (1992)). Alternatively, because the KAT packaging function and viral vector plasmids contain the SV40 origin of replication, they can be transfected into cell lines that enable replication of SV40 origin-containing plasmids due to expression of the SV40 T antigen, such as tsa201 (Heinzel et al., *J. Virol.* 62(10):3738-3746 (1988)). Using the KAT system, viral titers in the presence of plasmid replication are 3 to 10-fold higher than in the absence of replication. Whether replicating or nonreplicating plasmids are used, the KAT system permits the rapid production of high titer recombinant retrovirus supernatants without the need for generating stable producer lines.

The retroviral constructs of the invention also find use in the method of the invention to transduce by cocultivation, with high efficiency, mammalian cells, such as primary human cells, that are typically refractory to transduction by conventional means.

The plasmids of the invention also find use in the construction of stable cell lines that constitutively produce the retroviral proteins required in trans for the production of retrovirus particles: gag, pol and env. These stable packaging constructs can be introduced into human cell lines by calcium phosphate transfection or electroporation, together with a dominant selectable marker, such as neo, DHFR*, Gln Synthetase, ADA, followed by selection in the appropriate drug and isolation of clones. This enables the production of high titer stable producer clones following introduction of a retroviral construct into these cells. These cell lines have all of the same properties of the transiently transfected producer cells. However, due to stable integration of both packaging function and virus vector, they continue to produce high titer retrovirus indefinitely.

Plasmids containing the packaging functions can be split with one encoding the gag and pol genes and a second encoding the env gene product. Packaging lines containing two viral genomes have been described (Bosselman et al., *Molec. Cell. Biol.* 7(5):1797-1806 (1987); Markowitz et al., *J. Virol* 62(4): 1120-1124 (1988); Danos and Mulligan, *Proc. Natl. Acad. Sci. USA* 85:6460-6464 (1988)) and are desirable due to the significantly reduced chance for the generation of replication competent retrovirus (RCR) following recombination between a retroviral vector and packaging construct. Use of the plasmids of the invention results in a packaging line yielding the high efficiency transduction of the transient system, but with the added ease of a stable packaging system and the safety of a two genome packaging system. The novel plasmids of the invention enable a significant advance over previously described two genome packaging lines. The KAT plasmids encoding gagpol and env genes have been constructed so that only protein coding sequence from the retroviral genome is present. Using the retroviral vectors described in the invention, no overlap exists between the retrovirus vector and packaging genomes at their 3' ends. This structure in combination with replacement of the gag start codon (ATG) in the vector with a stop codon absolutely precludes the generation of replication competent retrovirus in contrast to previously described packaging lines where complete viral genomes containing mutations (Danos and Mulligan, *Proc. Nat'l. Acad. Sci. (USA)* 85:6460-6464 (1988)) or deletions (Bosselman et al., *Molec. Cell. Biol.* 7(5):1797-1806 (1987); Markowitz et al., *J. Virol.* 62(4): 1120-1124 (1988)). These prior known packaging lines contain overlap at the 3' end of the virus vector with the packaging line and can potentially generate RCR.

Two genome packaging lines are constructed by sequential introduction of the gagpol plasmid followed by the env-containing plasmid. The env genes are responsible for recognition of cell surface receptors. Five functionally and structurally different env genes have been identified in murine leukemia viruses and have been shown to have genetically distinct receptors (Battini et al., *J. of Virol.* 66:1468-1475 (1992)). Human host range with murine leukemia virus vectors is possible by the introduction of the amphotropic env gene into a cell line that expresses the ecotropic MLV gagpol (Danos and Mulligan, *Proc. Nat'l. Acad. Sci. USA* 85:6460-6464 (1988)). The xenotropic and 10A1 MLV viruses have human host range, as well as the gibbon ape leukemia and feline leukemia viruses. Using cDNA clones of these env genes, one or more can be stably introduced into a gagpol line to create a packaging line where the retrovirus produced following introduction of a retroviral vector can enter the target through multiple genetically distinct receptors. This leads to substantial increases in apparent viral titer. The vectors of the invention provide for the ability to create these types of novel packaging lines.

Most of the techniques used to construct vectors, and transfect and infect cells, are widely practiced in the art, and most practitioners are familiar with the standard resource materials which describe specific conditions and procedures. However, for convenience, the following paragraphs may serve as a guideline.

Construction of the vectors of the invention employs standard ligation and restriction techniques which are well understood in the art (see Maniatis et al., in *Molecular Cloning: A Laboratory Manual*, Cold Spring Harbor Laboratory, N.Y. (1982)). Isolated plasmids, DNA sequences, or synthesized oligonucleotides are cleaved, tailored, and religated in the form desired.

Site-specific DNA cleavage is performed by treating with the suitable restriction enzyme (or enzymes) under conditions which are generally understood in the art, and the particulars of which are specified by the manufacturer of these commercially available restriction enzymes. (See, e.g. New England Biolabs, Product Catalog.) In general, about 1 µg of plasmid or DNA sequences is cleaved by one unit of enzyme in about 20 µl of buffer solution. Typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods of Enzymology* 65:499-560 (1980).

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 minutes at 20° C. in 50 mM Tris (pH 7.6) 50 mM NaCl, 6 mM MgCl$_2$, 6 mM DTT and 5–10 µM dNTPs. The Klenow fragment fills in at 5' sticky ends but chews back protruding 3' single strands, even though the four dNTPs are present. If desired, selective repair can be performed by supplying only one of the dNTPs, or with selected dNTPs, within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 15–50 µl volumes under the following standard conditions and temperatures: 20 mM Tris-Cl pH 7.5, 10 mM MgCl$_2$, 10 mM DTT, 33 mg/ml BSA, 10 mM-50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 mM total end concentration). Intermolecular blunt end ligations (usually employing a 10–30 fold molar excess of linkers) are performed at 1 µM total ends concentration.

The retroviral vectors and packaging plasmids of the KAT system are prepared as follows:

Production of novel retroviral vectors and packaging plasmids

The KAT constructs include DNA packaging plasmids consisting of at least one retroviral helper DNA sequence derived from a replication-incompetent retroviral genome, e.g. a leukemia virus genome, encoding in trans all virion proteins required to package a replication incompetent retroviral vector, and for producing virion proteins capable of packaging the replication-incompetent retroviral vector at high titer, without the production of replication-competent helper virus. In one embodiment the retroviral packaging DNA sequence lacks the region encoding the native enhancer and/or promoter of the viral 5' LTR of the virus, and lacks the psi function sequence responsible for packaging helper genome as well as the 3' LTR, but encodes a foreign enhancer and/or promoter which directs efficient transcription in a cell type where virus production is desired, and includes an SV40 polyadenylation site. The transcription initiation site of the foreign enhancer and promoter is joined to the leukemia virus genome at the 5' end of the "R" region of the 5' LTR.

The retrovirus may be a Moloney Murine Leukemia Virus (MMLV), the Human Immunodeficiency Virus (HIV) or the Gibbon Ape Leukemia virus (GALV). The foreign enhancer and promoter joined to the R region of the 5' LTR may be the human cytomegalovirus (HCMV) immediate early (IE) enhancer and promoter (the U3 region) of the Moloney Murine Sarcoma Virus (MMSV), the U3 region of the Rous Sarcoma Virus (RSV), the U3 region of the Spleen Focus Forming Virus (SFFV), or the HCMV IE enhancer joined to the native Moloney Murine Leukemia Virus (MMLV) promoter.

All psi (ψ)-packaging plasmids are derivatives of the plasmid pIK1.1. pIK1.1 is a mammalian expression vector constructed by four successive insertions into pMF2, which is created by inserting the synthetic polylinker 5'-HindIII-SphI-EcoRI-AatII-BglI-XhoI-3' into KpnI and SacI sites of pSKII (Stratagene, San Diego, Calif.), with loss of the Kpn I and Sac I sites. First, a BamHI-XbaI fragment containing the SV40 T antigen polyadenylation site (nucleotides 2770 to 2533 of SV40, Reddy et al., *Science* 200:494–502 (1978)) and an NheI-SalI fragment containing the SV40 origin of replication (nucleotides 5725 to 5578 of SV40) are inserted by three-part ligation between the BglII and XhoI sites, with the loss of the BglII, BamHI, XbaI, NheI, SalI and XhoI sites. These BamHI-XbaI and NheI-SalI fragments are synthesized by PCR with pSV2neo (Southern and Berg, *J. Mol. Appl. Gen.* 1:327–341 (1982)) as the template using oligonucleotide primer pairs 3 and 4, and 5 and 6, respectively, which incorporated BamHI, XbaI, NheI and SalI sites at their respective ends. Second, an SphI-EcoRI fragment containing the splice acceptor of the human α1 globin gene second exon (nucleotides +143 to +251) is inserted between the SphI and EcoRI sites. This SphI-EcoRI fragment is synthesized by PCR with pπSVαHP (Treisman et al., *Proc. Natl. Acad. Sci. USA* 80:7428–7432 (1983)) as the template using oligonucleotide primers 7 and 8, which incorporate SphI and EcoRI sites at their respective ends. Third, the synthetic polylinker 5'-EcoRI-BglII-NcoI-ApaI-AatII-3' is inserted between the EcoRI and the AatII sites. Fourth, a HindIII-SacI fragment containing the CMV IE enhancer/promoter (nucleotides –674 to –19, Boshart et al., *Cell* 41:521–530 (1985)) and a chemically synthesized SacI-SphI fragment containing the CMV IE first exon/splice donor (nucleotides –19 to +170) are inserted by three-part ligation between the HindIII and SphI sites. The HindIII-SacI fragment is prepared by PCR with pCDM8 (Seed, *Nature* 329:840–842 (1987); Seed and Aruffo, *Proc. Natl. Acad. Sci. USA* 84:3365–3369 (1987)) as the template using oligonucleotide primers 9 and 10, which incorporated HindIII and SacI sites at their respective ends.

Primer 3: 5'-GGTCGACCTGGATCCGCCATACCAC-ATTTGTAG-3' (SEQ ID NO: 1)

Primer 4: 5'-GCCGCGGCTCTAGAGCCAGACATGA-TAAGATAC-3' (SEQ ID NO: 2)

Primer 5: 5'-AAGCTTGTGCTAGCTATCCCGCCCCT-AACTCCG-3' (SEQ ID NO: 3)

Primer 6: 5'-CGAAATCGGTCGACCGCAAAAGCCT-AGGCCTCC-3' (SEQ ID NO: 4)

Primer 7: 5'-GTCTATAGCATGCTCCCCTGCTCCGA-CCCG-3' (SEQ ID NO: 5)

Primer 8: 5'-GGTACCGAATTCTCCTGCGGGGAGA-AGCAG-3' (SEQ ID NO: 6)

Primer 9: 5'-CGCCAAGCTTGGCCATTGCATACGGT-3' (SEQ ID NO: 7)

Primer 10: 5'-GAGGTCTAGACGGTTCACTAAACG-AGCTCT-3' (SEQ ID NO: 8)

An Xba I site is introduced at the transcription initiation site of the HCMV IE promoter in pIK1.1 by replacement of the chemically synthesized Sac I/Sph I oligonucleotide encoding –19 to +170, described above, with a chemically synthesized Sac I/Sph I oligonucleotide where an Xba I site at nucleotides +1 to +6 had been introduced to generate pIK6.1. This allows insertion of any enhancer/promoter as a Hind III to Xba I cassette so as to insert the appropriate enhancer and promoter that will direct the highest possible expression level of the desired sequences in the desired cell type. In order to obtain the highest expression levels in mouse fibroblast NIH 3T3 (ATCC CRL 1658) or *M. dunni* (ATCC CRL2017), the complete MMSV U3 region was synthesized by PCR using the plasmid pN7 (Miller et al., *Mol. Cell. Biol.* 5:431–437 (1985)) as a template and two primers: one which encoded a HindIII site and the 5' 21 nucleotides of the U3, and a second which encoded the 3' 21 nucleotides of the MMLV U3 region and an Xba I site. This PCR fragment was cloned between the HindIII and Xba I sites of pIK6.1 to generate pIK6.1MMSV. In order to direct high level expression in human cells, pIK6.1MCV was constructed by isolation of the Nco I/Spe I fragment of the HCMV IE enhancer (Boshart et al., supra), addition of synthetic oligonucleotide Bcl I linkers, and insertion in the Bam HI site of the plasmid pΔHB (Dr. P. Robbins, University of Pittsburgh, Pittsburgh, Penn.). This plasmid was designated pMCV. pΔHB is a plasmid in which the ClaI to EcoRI fragment of pZIPneoSVX (Cepko et.al, supra), containing viral sequences including the 3' LTR, has been cloned into the ClaI and Eco RI sites of pBR322 and where the Sau 3AI to Hpa II enhancer fragment of MMLV U3 has been removed. Due to the homology between the MMLV U3 and the MMSV U3, the PCR primers described above were used to generate a Hind III/Xba I linker fragment encoding the U3 fragment of pMCV, which was cloned into pIK6.1 to generate pIK6.1MCV. These plasmids, as well as pIK6.1, were further modified by deletion of 112 nucleotides of the SV40 polyadenylation site between the ApaI site at the 3' end of the pIK polylinker and the Hpa I site in the SV40 polyadenylation site and replacement with an Nhe I linker to create pIK6.1.Nhe, pIK6.1.MMSV.Nhe and pIK.6.1MCV.Nhe.

pIK6.1MMSVampac and pIK6.1MCVampac were constructed by insertion of a 3813 base Sac I/Sal fragment encoding a portion of the U3 region, the R, and U 5 regions, the gag gene and a portion of the pol gene of pMOV psi- (Mann et al., supra), and the 4140 base pair Sal 1-Nhe I fragment encoding pol/env, derived from pCRIPamgag-2 (Dr. O. Danos, Institute Pasteur, Paris, France) between the Sac I and Nhe I sites of pIK6.1MMSV.Nhe or pKI6.1MCV.Nhe, respectively. pCRIPamgag-2 is a derivative of pCRIPamgag where the pBR322 plasmid backbone has been replaced by the plasmid pUC19. The resulting plasmids encode the gag and pol genes from ecotropic MMLV and the envelope gene from the 4070A amphotropic MLV (Chattopadhyay et al., *J. Virol.* 39(3):777–791 (1981)) and are diagramed in FIG. 1.

To delete untranslated sequences 3' from the envelope gene of pIK6.1MCVampac a PCR reaction was performed using pIK6.1MCVampac as the template with synthetic oligonucleotides 5' CTGATCTTACTCTTTGGACC3' (SEQ ID NO: 31) and 5' GAATTCGCTAGCCTATGGCTCG-TACTCTATAG 3' (SEQ ID NO: 32). The resulting 142 basepair PCR product was cut with ClaI and NheI. This 100 base pair fragment was excised and used to replace the corresponding 172 base pair ClaI to NheI fragment of pIK6.1MCVampac to give pIK6.1MCVampac UTΔ.

pIK6.1amenvATGUTΔ was constructed by replacing the 172 base pair ClaI to NheI fragment in pIK6.1amenvATG with the 100 base pair ClaI to NheI fragment from pIK6.1MCVampacUTΔ. pIK6.1MCVamenvATGUTΔ was constructed by replacing the 961 base pair Hind III to Eco RI fragment containing the CMV promotor and alpha globin splice acceptor in pIK6.1amenvATGUTΔ with the corresponding 896 base pair Hind III to Eco R1 fragment from pIK6.1MCV.

pIK6.1MCVgagpolATG was constructed by replacing the 961 base pair Hind III to Eco RI fragment containing the CMV promotor and alpha globin splice acceptor in pIK6.1gagpolATG with the corresponding 896 base pair Hind III to Eco R1 fragment from pIK6.1MCV.

The retroviral packaging plasmids of the invention, designated pIK6.1MMSVampac and pIK6.1MCVampac, have been deposited with the American Type Culture Collection (ATCC), 12301 Parklawn Drive, Rockville, Md., under the Budapest Treaty, and have there been identified as follows:

| Plasmid | ATCC Accession No. | Deposit Date |
|---|---|---|
| pIK6.1MMSVampac | 75484 | June 11, 1993 |
| pIK6.1MCVampac | 75483 | June 11, 1993 |

In another embodiment, the packaging functions may be encoded by two plasmid based expression vectors, for example two helper sequences, where a first helper sequence contains a cDNA encoding the gag and pol proteins of ecotropic MMLV and a second helper sequence contains a cDNA encoding a retroviral env protein. The Env gene, which determines the host range, may be derived from the genes encoding the xenotrophic, amphotrophic, ecotrophic, polytropic (mink focus-forming) or 10A1 murine leukemia virus, Gibbon Ape Leukemia Virus (GALV), the Human Immunodeficiency Virus (gp160) env proteins; the Vesicular Stomatitus Virus (VSV) G protein; the Human T cell leukemia (HTLV) type I and II env gene products; a chimeric envelope gene derived from combinations of one or more of the aforementioned env genes; or chimeric envelope genes encoding the cytoplasmic and transmembrane of the aforementioned env gene products and a monoclonal antibody directed against a specific surface molecule on a desired target cell.

Construction of plasmids which reflect this embodiment is described as follows: pIK6.1gagpolATG, encoding the MMLV gag and pol genes, was constructed first by digestion of pMOVpsi- with Sca I, addition of a Nhe I synthetic linker, redigestion with Afl II and isolation of the 5.2 kb Afl II/Nhe I fragment (nucleotides 644 to 5869 of MMLV). A synthetic oligonucleotide encoding nucleotides 621 to 644 of MMLV (ATG of the gag gene to Afl II), in which the ATG at nucleotide 621 was converted to a Nco I site, was ligated together with the Afl II/Nhe I fragment between the Nco I site polylinker and the Nhe I site at the 5' end of the SV40 poly adenylation site of pIK6.1Nhe.

pIK6.1amenvATG, encoding the MLV 4070A Env gene, was constructed by digestion of pCRIPAMGAG-2 (Danos and Mulligan, supra) with Afl 111 and redigestion with either Nhe1 or HinP1 and isolation of the 0.325 kb HinP 1/Afl 111 fragment (nucleotides 37 to 365 of the MLV 4070A Env gene; (Ott et.al., *J. Virol.* 64(2):757–766(1990)) and the 1.7 kb Afl 111/Nhe 1 fragment (from nucleotide 365 of the MLV 4070A Env gene; (Ott et.al., supra) to the Nhe 1 site in the MMLV 3' LTR of pCRIPAMGAG-2 (Danos and Mulligan, supra) respectively. A synthetic oligonucleotide encoding nucleotides 37 to 43 of the MLV 4070A Env gene (ATG of the env gene to HinP 1), in which the ATG at nucleotide 37 was converted to a Nco I site, was ligated together with the HinP 1/Afl 111 fragment and the Afl 111/Nhe 1 fragment between the Nco I site in the polylinker and the Nhe I site at the 5' end of the SV40 poly adenylation site of pIK6.1Nhe. These plasmids are diagramed in FIG. 1.

The two genome retroviral packaging plasmids of the invention, designated pIK6.1gagpolATG and pIK6.1amenvATG, have been deposited with the American Type Culture Collection (ATCC), 12301 Parklawn Drive, Rockville, Md., under the Budapest Treaty, and have there been identified as follows:

| Plasmid | ATCC Accession No. | Deposit Date |
|---|---|---|
| pIK6.1gagpolATG | 75486 | June 11, 1993 |
| pIK6.1amenvATG | 75485 | June 11, 1993 |

Retroviral Vectors

Both single genome and two genome packaging constructs utilize retroviral vectors that contain modified 5'

LTRs that direct efficient transcription in the cell type where retrovirus is to be produced. The retroviral vectors of the invention are modeled after pZen (Johnson et al., *The EMBO Journal* 8(2):441–448 (1989)), a neo-version of pZIP-neoSVX (Cepko et al., *Cell* 37:1053–1062(1985)), in which the gene product to be expressed is cloned downstream of the splice acceptor in the position normally occupied by the neo cassette (Cepko et al., supra). In addition, viral gag sequences up to the Nar I site of MMLV (nucleotide 1038) were added for improved packaging (Armentano et al., *J. Virol.* 61:11647–1650 (1987)) and the Xho I to Cla I fragment of pZIPneoSVX was deleted (Cepko et al., supra). The Eco RI to Apa I polylinker from pIK1.1 was inserted downstream of the splice acceptor to enable transfer of inserts from pIK plasmids into retroviral constructs. The resulting plasmid is designated pRTD1.2 and contains both 5' and 3' MMLV LTRs. The 5' LTR U3 region of pZIP-neoSVX was replaced with the MMSV U3, derived from the HindIII/Sac I fragment of pIKMMSV, to generate pRTD4.2. In pRTD2.2, the U3 region of the 5' LTR of pZIPneoSVX was replaced with the Hind III/Sac I fragment from pIK1.1 encoding the CMV immediate early enhancer/promoter, which was fused to the MMLV R region by an oligonucleotide that encodes nucleotides 19 (Sac I) to +1 of the HCMV promoter linked to nucleotides +1 to +32(KpnI) of MMLV (Schinnick et al., *Nature* 293:543–548 (1980)). pRTD2.2SVG was constructed by replacement of the (750 bp) Sac I to Bst EII fragment of pRTD2.2 with the (736 bp) Sac I to Bst EII fragment of LXSN (Miller and Rosman, *BioTechniques* 7:980–990(1989)). pRTD2.2SSA was constructed by replacement of the (1441 bp) Sac I to Eco RI fragment of pRTD2.2 with the (1053 bp) Sac I to Eco RI fragment of LXSN (Miller and Rosman, supra). pRTD2.2SVGE- was constructed by synthesis of an oligonucleotide encoding nucleotides 2878–2955 of pLXSN (GenBank Accession Bank, M28248) which had been appended by addition of an Apa I site on it's 5' end. This was used to replace the Apa I to Nhe I fragment of pRTD2.2SVG, which contains the DNA sequence 3' of the of the polylinker and 5' of the Nhe I site in the 3' LTR. These retroviral vector constructs of the invention have a pBR322 backbone and include pRTD2.2, pRTD4.2, pRTD2.2SVG, pRTD2.2SVGE- and pRTD2.2SSA.

In order to permit plasmid replication in cells which express the SV40 T antigen, the sequences between the 5' and 3' LTRs of pRTD2.2 were cloned between the SacI and Eco RI sites of pIK1.1, described above, which contains the SV40 origin of replication to form vector pIKT2.2. pIKT2.2SVG was constructed by insertion of the fragment defined at its 5' end by the Sac I site in the HCMV promoter of pRTD2.2SVG and defined at its 3' end by an Eco RI site located 750 bp downstream of the 3' LTR of pRTD2.2SVG, between the SacI and Eco RI sites of pIK1.1. pIKT2.2SVGE-F3 was constructed by replacing the 182 base pair ApaI to NheI fragment of pIKT2.2SVGF3 with the 80 base pair ApaI to NheI fragment from pRTD2.2SVGE-F3 as described above.

pRT43.2F3 was derived from pIKT2.2SVGE-F3 by replacing the Eco RI to ApaI polylinker located approximately 750 base pairs downstream from the 3' LTR with a synthetic oligonucleotide containing an AscI recognition site. In addition, the Nde I site at the 3' end of the viral gag sequences has been converted to an XhoI site by oligonucleotide insertion. pRT43.3PGKF3 was derived from pRT43.2F3 first by removal of the 3' LTR in pRT43.2F3 and insertion of a 3' LTR in which the sequences from PvuII to XbaI were deleted (MMLV, GenBank session #J02255 nucleotide numbers 7938–8115). In addition the MMLV splice acceptor region has been replaced with the human phosphoglycerate kinase gene promotor (GenBank session #M11958 nucleotides 2–516) which was cloned into a polylinker with a XhoI site at its 5' end and an Eco RI at its 3' end.

In one embodiment of the retroviral vectors of the invention, DNA encoding genes to be transduced into mammalian target cells using the method of the invention, for expression of chimeric receptor constructs are prepared. The construction of the chimeric receptor constructs is described below.

CD4/CD3 zeta and Anti-HIV/CD3 zeta Retroviral vectors

KAT retroviral vectors pRTD2.2F3, pRTD2.2SVGF3, pRTD2.2SSAF3, pRTD2.2SVGF3E-, pIKT2.2SVGF3 were constructed by Eco RI/Apa I digestion of pIKF3 (described below), isolation of the 1.9 kb fragment, followed by ligation of this fragment between the Eco RI and Apa I sites in the pIK polylinker of the vectors pRTD2.2, pRTD2.2SVG, pRTD2.2SSAF3, pRTD2.2SVGE-, pIKT2.2SVG. KAT retroviral vector pRTD2.2F15 was constructed by Eco RI/Apa I digestion of pIKF15neo (described below), isolation of the 2.2 kb fragment, followed by ligation of this fragment between the Eco RI and Apa I sites in the pIK polylinker of the vector pRTD2.2. These vectors encode a chimeric molecule containing the extracellular domain of human CD4 (F3 derivatives) or a single chain antibody against gp41 of HIV (F15 derivatives), respectively, fused to the cytoplasmic domain of the CD4 receptor (amino acids 372–395 of the mature CD4 chain) and the transmembrane domain of the CD3-complex associated-gene zeta (ζ) (amino acids 372–395 of the mature zeta chain). Chimeric receptor cassettes encoding either the extracellular domains (residues 1–371 of the mature CD4 protein) of the human CD4 receptor (designated F3) or a single chain antibody to HIV gp41 derived from a human antibody (98.6) specific for the gp41 moiety of the HIV envelope protein (designated F15) were fused to the CD3 ζ chain and cloned between the Eco RI and Apa I sites of pIK1.1 described above. In the single-chain antibody, the variable domains of both the heavy and light chain genes were covalently linked via a peptide tether, to create an antigen binding site on a single molecule.

A more detailed description of the construction of the chimeric receptors follows.

Construction of CD4-zeta Chimeras

Plasmid pGEM3zeta bears the human zeta cDNA (Weissman et al., *Proc. Natl. Acad. Sci. USA* 85:9709–9713 (1988). The plasmid pBS.L3T4 bears the human CD4 cDNA (Littman and Gettner, *Nature* 325:453–455 (1987)). A BamHI-ApaI restriction fragment (approximately 0.64 kb) encompassing the entire human zeta chain coding sequence from residue 7 of the extracellular (EXT) domain, was excised from pGEM3zeta, and subcloned into the BamHI and ApaI restriction sites of the polylinker of pBluescript II SK (+) 9pSK is a phagemid based cloning vector from Stratagene (San Diego, Calif.), generating pSK.zeta. Subsequently, a BamHI restriction fragment encompassing the entire CD4 coding sequence (approximately 1.8 kb) was excised from pBS.L3T4, and subcloned into the BamHI site of pSK.zeta, generating pSK.CD4.zeta.

Single-stranded DNA was prepared from pSK.CD4.zeta (Stratagene pBluescript II protocol), and used as a template for oligonucleotide-mediated directional mutagenesis (Zoller and Smith, *Nucleic Acids Res.* 10:6487–6500 (1982)) in order to generate CD4-zeta chimeras with the desired junctions described below. CD4-zeta fusions 1, 2, and 3 were subsequently sequenced via the Sanger dideoxynucleotide technique (Sanger et al., *Proc. Natl. Acad. Sci.* 74:5463–5467 (1977)), excised as EcoRI-ApaI restriction fragments, and cloned into the polylinker of expression vector pIK.1.1 or pIK.1.1.Neo at identical sites.

An EcoRI-BamHI restriction fragment (approximately 1.8 kb) encompassing the entire coding region of CD4 was excised from pSK.CD4.zeta, and subcloned between the EcoRI and BglII sites of the pIK.1.1 or pIK.1.1.Neo polylinker.

The plasmid pUCRNeoG (Hudziak, et al., *Cell* (1982) 31:137–146) carries the neomycin gene under the transcriptional control of the Rous Sarcoma virus (RSV) 3' LTR. The RSV-neo cassette was excised from PURCNeoG as a HincII restriction fragment (approximately 2.3 kb), and subcloned between the two SspI sites of pIK.1.1, generating pIK.1.1.Neo.

The CD4-zeta chimeric receptor F3 was constructed from the extracellular (EC) and cytoplasmic (CYT) domains of CD4 and zeta respectively. The transmembrane (TM) domain of this receptor was derived from CD4. F3 retains the CD4 EXT domain comprising all four V domains (residues 1–371 of the mature CD4 protein), the TM domain of CD4 (residues 372–395 of the mature CD4 chain), and the CYT domain of zeta (residues 31–142 of the mature zeta chain).

Preparation of Single Chain Antibody-Zeta Chimeric Receptor

Construction of expression vector encoding the heavy chain of human monoclonal antibody (mAb) 98.6:

To direct the expression of the heavy chain of human mAb 98.6 (S. Zolla-Pazner, *Proc. Natl. Acad. Sci.* (1989) 86:1624–1628), the plasmid pIK.98.6-γFL was constructed. A full length IgG1 heavy chain cDNA was generated by reverse transcription of 5 µg of total RNA from the cell line SP-1/98.6 (Zolla-Pazner, supra using oligo-dT as the primer, followed by PCR using oligonucleotide primers 17 and 2 (see below). The 1.5 kb Eco RI to Bgl II fragment was cloned between the Eco RI and Bgl II sites of pIK1.1. To ensure that the heavy chain would be of the desired allotype, the Kas I-Bgl II fragment of the cDNA was replaced with a 0.94 kb Kas I-Bgl II fragment from pIK.Cγ1. pIK.Cγ1 was constructed by the insertion of a cDNA coding for the constant region of IgG1 heavy chain obtained by PCR using DNA from a human spleen cDNA library (Clontech, Inc., Palo Alto, Calif.) as substrate and oligonucleotide primers 2 and 18 (see below), between the Eco RI and Bgl II sites of pIK1.1.

Construction of expression vector encoding the light chain of human monoclonal antibody (mAb) 98.6:

To direct the expression of the light chain of mAb 98.6, the plasmid pIK.98.6κFL was constructed. A full length IgG1 light chain cDNA was generated by reverse transcription of 5 µg of total RNA from the cell line SP-1/98.6 using pdN$_6$ (Pharmacia/LKB) as the primer, followed by PCR with primers 19 and 20 (see below). The 0.78 kb fragment was then cut with Eco RI and Bgl II and cloned between the Eco RI and Bgl II sites of pIK1.1.

Construction of expression vector encoding SAb derived from the heavy and light chains of mAb 98.6:

a) Construction of pIK98.6-K/L/H:

To direct the expression of a single-chain antibody (SAb) form of mAb 98.6, pIK.98.6-K/L/H was constructed. The SAb expressed consists of the secretion leader sequence and amino acids 1–107 of the mature 98.6 mAb light chain variable ($V_L$) region fused to a 14 amino acid linker of the sequence GSTSGSGSSEGKG (SEQ ID NO: 9) (L212, Betzyk et al., *J. Biol. Chem.* (1990) 265:18615–18620), which in turn was fused to amino acid 1 of the mature 98.6 mAb heavy chain $V_H$ region. This was then fused at amino acid 113 to amino acid 234 of the IgG1 heavy chain constant region, in order to delete the CH1 domain of the IgG1 heavy chain constant region for improved secretion. pIK.98.6-K/L/H was constructed in three steps.

First, deletion mutagenesis was performed to fuse amino acid 113 of the $V_H$ region of mAb 98.6 to amino acid 234 of the IgG1 heavy chain, using the single stranded template form of pIK.98.6-γFL as the template and oligonucleotide 21 as the primer (see below). Correctly deleted plasmids were found using oligonucleotide 22 as a probe (see below). This plasmid is referred to as pIK.H/Fc-int. To fuse amino acid 107 to the amino terminus of the linker peptide, the $V_L$ region of the mAb 98.6 light chain was generated by PCR using pIK.98.6-κFL as substrate and oligonucleotides 23 and 24 as primers (see below). This was done to place a Sal I site at the 3' end of the $V_L$ sequence, without altering the amino acid sequence of the resulting protein. This fragment, together with oligonucleotides 25 and 26 (see below) was ligated between the EcoRI and Bgl II sites of pIK1.1, generating the plasmid pIK.K/L-int.

In the final step, the 0.45 kb fragment of pIK.K/L-int was cloned between the Eco RI and Kpn I sites of pIK.H/Fc-int., generating plasmid pIK.K/L/H-int. Single-stranded DNA from this plasmid was used as template and oligonucleotide 27 was used as primer (see below) to fuse the carboxy-terminal amino acid of the linker to amino acid 1 of the $V_H$ region of mAb 98.6 by deletion mutagenesis. Correctly deleted plasmids were found using oligonucleotide 28 as a probe (see below). The resulting plasmid is pIK.98.6K/L/H.

b) Construction of pIK.CD4γ2:

The plasmid pIK.CD4γ2 was constructed to direct the expression of a fusion protein composed of the secretion leader and the first 180 amino acids of the mature CD4 antigen fused to amino acid 234 of the human IgG2 heavy chain constant region and thus containing part of the hinge and all of the CH2 and CH3 domains. This deletes the CH1 domain of the IgG2 heavy chain for improved secretion. pIK.CD4γ2 was constructed by generating a fragment containing the Fc portion of the human IgG2 heavy chain by PCR using DNA from a human spleen cDNA library (Clontech) as substrate and oligonucleotides 3 and 4 as the primers. The 0.75 kb Nhe I to Bgl II fragment generated was ligated together with the 0.6 kb Eco RI to Nhe I fragment from pSKCD4ζ between the Eco RI and Bgl II sites of pIK1.1.

c) Construction of pIK.F5:

The plasmids pIK.F7 was constructed to direct expression of several versions of CD4/IgG/zeta (ζ) fusion proteins which all contain a human membrane-bound IgG membrane hinge domain (Tyler et al. (1982) *Proc. Natl. Acad. Sci.* 79:2008–2012). Each protein to be expressed contained amino acids 1–180 of CD4 receptor, followed by amino acids 234–445 of human IgG2 heavy chain constant region, followed by the 18 amino acid M1 membrane hinge domain of human IgG3 (Bensmana and Lefranc, (1990) *Immunogenetics* 32:321–330), followed by a transmembrane domain, followed by amino acids 31–142 of the human ζ chain. pIK.F7 contains the transmembrane domain (amino acids 372–395) of CD4.

To construct this plasmid, the first step was cloning the human IgG3 M1 exon (Bensmana and Lefranc, supra). This was done by generating a 0.13 kb Bam HI to Bgl II fragment containing the M1 exon by PCR using DNA from the human cell line W138 as substrate and oligonucleotides 7 and 8, and cloning it into the Bgl II site of pIK.CD4γ2. The resulting plasmid is referred to as pIK.CH3/M1-int. Single stranded DNA from this plasmid was used as template and oligonucleotide 9 was used as the primer to fuse amino acid 445 of human IgG2 to the first amino acid of the IgG3 membrane hinge domain by deletion mutagenesis. The fusion is designed to generate the sequence found at the natural junction between CH3 and M1 in membrane-bound IgG molecules. Correctly deleted clones were found using oligonucleotide 10 as a probe. The resulting plasmid is referred to as pIK.CD4γ2/M1.

pIK.CD4γ2/M1 was cut with Bgl II and blunted with T4 polymerase, then cut with Nhe I. The resulting 0.83 kb fragment was ligated together with the 1.3 kb Pvu II to Apa I fragment from pIK.F3 between the Nhe I and Apa I sites of pIK.CD4γ2 to generate the plasmid pIK.F7-int. Single stranded DNA from this plasmid was used as template and oligonucleotide 15 was used as the primer to fuse the last amino acid of the IgG3 M1 membrane hinge domain to amino acid 372 of CD4 by deletion mutagenesis. Correctly deleted clones were found by using oligonucleotide 16 as a probe. The resulting plasmid is pIK.F7.

The oligonucleotides used as primers and probes as described above were as follows:

Oligonucleotides

2. CGGAGATCTCGTGCGACCGCGAGAGCC (SEQ ID NO: 10)
3. GGAATTCGCTAGCTTTCCAGGAGCGCAAATGTTGTGTC (SEQ ID NO: 11)
4. CGGAGATCTC(A/G)CGCGACCCCGAGAGCC (SEQ ID NO: 12)
7. CGGGATCCAGAGCTGCAACTGGAG (SEQ ID NO: 13)
8. GAAGATCTGACCTTGAAGAAGGTGAC (SEQ ID NO: 14)
9. TCTCCTCCAGTTGCAGCTCCGGAGACAGGGAGAGGC (SEQ ID NO: 15)
10. TTGCAGCTCCGGAGAC (SEQ ID NO: 16)
15. CAGCACAATCAGGGCCATGTCCAGCTCCCCGTCCTG (SEQ ID NO: 17)
16. AGGGCCATGTCCAGCT (SEQ ID NO: 18)
17. CGGAATTCGGTACCTCCTGTGCAAGAAC (SEQ ID NO: 19)
18. CGGAATTCGCCTCCACCAAGGGCCCA (SEQ ID NO: 20)
19. CGGAATTCACGCGTCCCAGTCAGGACACAGC (SEQ ID NO: 21)
20. GAGAGAGATCTGCTAGCGGTCAGGCTGGAACTGAG (SEQ ID NO: 22)
21. GCATGTGTGAGTTTTGTCTGAGGAGACGGTGACCAG (SEQ ID NO: 23)
22. GTTTTGTCTGAGGAGA (SEQ ID NO: 24)
23. GTGACAGTCGACCCCTTGAAGTCCACTTTGGT (SEQ ID NO: 25)
24. CCACCCCTCACTCTGCTTCTC (SEQ ID NO: 26)
25. TCGACCAGCGGCAGCGGCAAGAGCAGCGAGGGTAAGGGTACCA (SEQ ID NO: 27)
26. GATCTGGTACCCTTACCCTCGCTGCTCTTGCCGCTGCCGCTGG (SEQ ID NO: 28)
27. CTCCTGTAGTAGCACCTGACCCTTACCCTCGCTGCT (SEQ ID NO: 29)
28. AGCACCTGACCCTTAC (SEQ ID NO: 30)

Construction of pIK.F15neo

To direct the expression of a fusion protein consisting of the K/L/H SAb form of mAb 98.6 linked at amino acid 445 of the IgG1 heavy chain to the 18 amino acid IgG3 M1 membrane hinge, which was in turn fused to the CD4 transmembrane domain (amino acids 372–395) and ζ cytoplasmic domain (amino acids 31–142), pIK.F15neo was constructed by inserting the 1.5 kb Nsi I fragment of pIK.98.6-K/L/H between the Nsi I sites of pIK.F7neo and a clone of the correct orientation was selected.

Production of Retrovirus in mammalian cells

Single or double genome KAT packaging plasmids, for example pIK6.1MMSVampac, pIK6.1MCVampac, or pIK6.1amenvATG and pIK6.1gagpolATG (all described above), together with KAT retroviral constructs, for example, but not limited to pRTD2.2F3, pRTD2.2SVGF3, pRTD2.2SSAF3, pRTD2.2SVGF3E-, pIKT2.2SVGF3, pRTD2.2F15 (as described above), prepared as described above, are introduced into mammalian cells that can produce virus by standard means such as calcium phosphate cotransfection (Wigler et al., Proc. Natl. Acad. Sci. USA 76:1373–1377 (1979)). Mammalian cells that can produce virus and that may be transfected by the KAT constructs of the invention include, but are not limited to, human embryonic kidney cells such as 293 cells, tsa201 cells, mouse 3T3 mouse fibroblasts, M. dunni fibroblasts, and African green monkey kidney (COS) cells. Transfected cells are assayed for surface expression of the chimeric receptor by FACS to verify that DNA constructs have been successfully introduced.

Viral supernatants are harvested using standard techniques such as filtration of supernatants 48 hours post transfection. The viral titer is determined by infection of $10^6$ NIH 3T3 cells with an appropriate amount of viral supernatant, in the presence of 8 µg/ml polybrene (Sigma Chemical Co., St. Louis, Mo.). 48 hours later, the transduction efficiency of the 3T3 cells is assayed by both FACS analysis and Southern blotting.

High Efficiency Transduction of target cells

In the method of the invention the KAT constructs of the invention are further used to transduce mammalian target cells with a foreign gene at high efficiency by cocultivation of KAT transfected cells with the mammalian target cells. In a preferred embodiment, desired virus producing cells, such as 293 cells, are transfected with the appropriate KAT constructs, then 24 hours post transfection, the transfected 293 cells are cocultivated for 48 hours with the purified mammalian target cells, such as CD8+ T cells. The target cells are harvested using standard procedures, expanded and tested for transduction efficiency, by well-known techniques such as flow cytometry or Fluorescence-activated Cell Sorter (FACS) analysis and Southern blot DNA analysis. Transduction efficiency is defined as the percentage of positive transduced cells as measured by FACS or Southern blot analysis compared to controls.

Using the KAT constructs transfected into human 293 cells to produce virus, a from 5 to 50-fold increase in viral titer as determined by supernatant infection of established cell lines, such as 3T3, is obtained, when compared to virus produced by the previously described COS transient virus production system (Landau and Litman, supra). In addition, primary human cells such as hematopoietic stem cells and human T cells, are transduced at levels 3 to 20-fold greater by cocultivation with KAT plasmid transfected 293 cells, than traditional packaging lines such as PA317 (Miller and Buttimore, supra).

While not wishing to be bound by any particular theory of the invention, it is believed that the high efficiency transduction of human target cells obtained using the method of the invention is mediated by cell-cell contact of the retrovirally infected human 293 cells with the target cells. The component of human 293 cells which effects high efficiency transduction of various target cells is expected to be a protein or lipid synthesized by the 293 cells. To determine the active component of this system, the membrane proteins and lipids of 293 cells are purified using known procedures and the ability of various purified components is tested for its ability to effect the transduction efficiency of the target cells. Once the active component is identified it can be synthesized by recombinant DNA or chemical technique. These synthesized components may be incorporated into virus particles to enhance the transduction efficiency of supernatants.

Suitable target cells are any mammalian cells of interest, and include, but are not limited to lymphocytes, particularly cytotoxic T cells, human hematopoietic stem cells, fibroblasts, epithelial cells, endothelial cells, myoblasts, retinal epithelial cells, islets of Langerhans, adrenal medulla cells, osteoblasts, osteoclasts, neurons, glial cells, ganglion cells, embryonic stem cells, and hepatocytes.

The genes which may be introduced into the target cells include, but are not limited to genes encoding chimeric receptors for signal transduction in lymphocytes, such as those described in copending U.S. patent application Ser. No. 988,194, filed Dec. 9, 1992, now U.S. Pat. No. 5,359,046, the disclosure of which is incorporated in its entirety herein by reference; growth factors, such as G-, M- and GM-colony stimulating factor (CSF), epidermal growth factor, platelet derived growth factor, transforming growth factor (TGF) and stem cell growth factor (SCF); lymphokines such as the interleukins; hormones such as ACTH, somatomedin, insulin, angiotensin; and coagulation factors, such as Factor VIII and Factor IX; the Multidrug Resistance Drug (MDR) gene; human adenosine deaminase (ADA); glucose cerebrosidase; the normal β-globin gene and erythopoietin (EPO).

The following examples are presented to illustrate the present invention and to assist one of ordinary skill in making and using the same. The examples are not intended in any way to otherwise limit the scope of the disclosure or the protection granted by Letters Patent hereon.

EXAMPLE I

Transient Production of High Titer Recombinant Retrovirus

Cell growth transfection and infection of established cell lines

Human embryonic kidney cells, designated 293 cells (ATCC CRL 1573, ATCC, Rockville, Md.) cells were grown in DMEM (JHR Biosciences, Lenexa, Kans.), 1 g/l glucose, 10% Donor calf serum (Tissue Culture Biologics, Tulare, Calif.) and split 1:10 every 3 days. 3T3 (ATCC CRL1573) cells were grown in DMEM (JHR Biosciences), 4.5 g/l glucose, 10% Donor calf serum (Tissue Culture Biologics) and split 1:10 every 3 days. COS (ATCC CRL1650) cells were grown in DME/F12 (GIBCO, Grand Island, N.Y.), 10% fetal bovine serum (Tissue Culture Biologics, Tulare, Calif.) and split 1:10 every 3 days. tsa201 cells, a derivative of 293s which contain the temperature sensitive mutant of the SV40 T antigen co-transfected with the neomycin resistance gene (Heinzel et al., *J. Virol.* 62(10):3738–3746 (1988)), were grown in DME/F12 (GIBCO), 10% fetal bovine serum (Tissue Culture Biologics) and split 1:10 every 3 days. 293 cells and tsa201 cells were plated 1×10$^6$ and 0.5×10$^6$ cells per 10 cm plate, respectively, 48 hours prior to transfection. COS and 3T3 cells were plated at 0.5×10$^6$ cells per 10 cm plate 24 hours prior to transfection. 10 μg of each plasmid, alone or in various combinations, was transfected by calcium phosphate coprecipitation (Wigler et al., supra) for all cell types. 24 hours following transfection, the media was changed. 24 hours later, viral supernatants were harvested and filtered through a 0.45 μm filter and flash frozen on dry ice. 3T3 cells were plated at 0.5×10$^6$ cells per 10 cm plate 24 hours prior to infection. Infections were carried out in 5 ml of media containing viral supernatant and 8 μg/ml polybrene (Sigma Chemical Co., St. Louis, Mo.). 24 hours following infection, the media was changed to polybrene-free media and the cells were grown for an additional 24 hours.

293 cells produced high titer retrovirus following transient transfection 293 cells were assayed for their ability to transiently produce recombinant retrovirus upon cotransfection with either the KAT packaging plasmid(s) pIK6.1MCVampac or pIK6.1amenvATG and pIK6.1gagpolATG,and the retroviral vectors pRTD2.2F3, pRTD2.2SVGF3, pRTD2.2SSAF3, pRTD2.2SVGF3E-, pIKT2.2SVGF3, and pRTD2.2F15, encoding the F3 or F15 chimeric receptors, by harvesting viral supernatants 48 hours post transfection, followed by infection of mouse 3T3 cells, and FACS analysis 48 hours later.

For FACS analysis, infected 3T3 cells are removed from the culture dish in the absence of trypsin and are processed for FACS analysis after incubation in 40 mM Tris, pH 7.5, 150 mM NaCl, 1 mM EDTA. Cells are washed 1× with phosphate buffered saline (PBS) plus 2% (FCS) fetal calf serum (Hyclone), followed by incubation with the appropriate FITC-conjugated detection antibody in the presence of PBS plus 2% FCS at a density of 1×10$^6$/ml for 30 minutes at 40° C. The cells are washed 3× with PBS plus 2% FCS, and finally resuspended in 0.5 ml PBS and analyzed by flow cytometry.

Figure 2D:
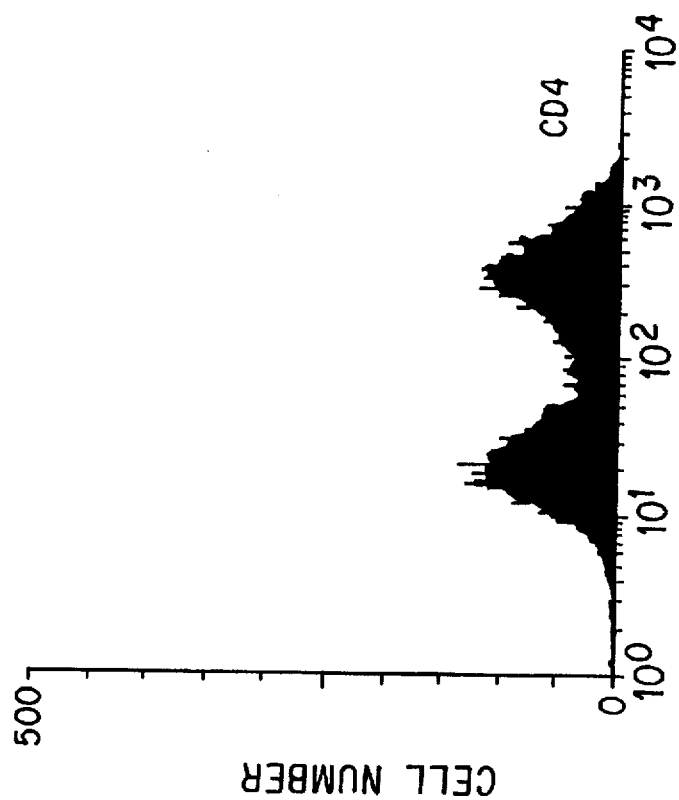
FIG. 2 (Parts A–D) shows the FACS profile of 293 cells transfected with retroviral constructs, as described in Example I, infra.
Figure 2C:
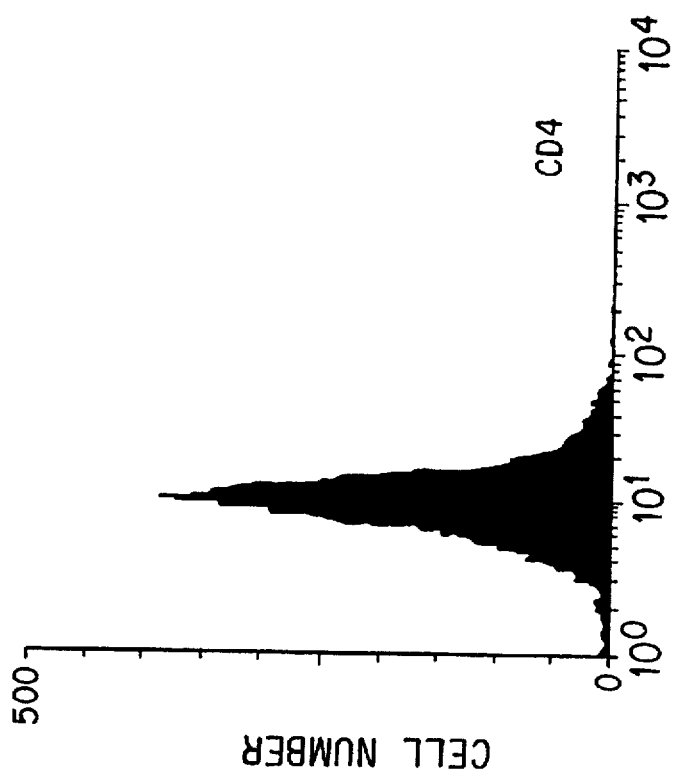

The results of FACS analysis are shown in FIG. 2. 293 cells cotransfected pIK6.1ampac and pRTD2.2F3 express high levels of F3 on their surface (FIG. 2B), compared to mock (control) transfected cells (FIG. 2A). 3T3 cells infected with viral supernatants harvested from transfected 293 cells revealed two well separated peaks corresponding to uninfected and infected 3T3 cells (FIG. 2D), which was significantly different compared to the FACS profile of transfected 293 cells (FIG. 2B) or mock infected 3T3 cells (FIG. 2C).

Table 1 demonstrates that cotransfection of KAT packaging plasmids and KAT retroviral constructs results in the production of high titer viral supernatants 48 hours following transfection, as assayed by 3T3 infection and FACS analysis. Cotransfection of pIK6.1ampac and pRTD2.2F3 yields viral supernatants that transduce 50% of the 10$^6$ 3T3 cells initially present at the time of infection. In contrast, virus produced by transient cotransfection in COS cells, as described by Landau and Litman (Landau and Litman, supra) was 10-fold less than the titers described by cotransfection of KAT plasmids into 293 cells. Virus production is highly reproducible in four transfection experiments, where duplicate 3T3 infections were carried out. In contrast, no detectable 3T3 infection is observed following transfection of the retroviral construct pRTD2.2F3 alone, demonstrating that viral production is dependant upon the presence of the packaging construct and the retroviral vector. High titer virus production is also dependant upon the presence of the retroviral construct. Transfection of pIKF3 expression vector alone, or cotransfection of pIKF3 expression vector and pIK6.1MMSVampac yields supernatants that fail to transduce 3T3 cells.

TABLE 1

| Construct | Packaging Function | % Transfection | % 3T3 Transduction |
|---|---|---|---|
| pRTD2.2F3 | — | 52 | 0/0 |
| pRTD2.2F3 | — | 55 | 0/0 |
| pRTD2.2F3 | pIK6.1MCVampac | 80 | 49/50 |
| pRTD2.2F3 | pIK6.1MCVampac | 85 | 50/49 |
| pRTD2.2F3 | pIK6.1MCVampac | 83 | 47/43 |
| pRTD2.2F3 | pIK6.1MCVampac | 85 | 49/48 |
| pRTD2.2F3 | pIK6.1gagpolATG, pIK6.1amenvATG | 78 | 27/77 |
| pRTD2.2F3 | pIK6.1gagpolATG, pIK6.1amenvATG | 78 | 25/26 |
| pIKF3 | — | 67 | 0/0 |
| pIKF3 | — | 59 | 0/0 |
| pIKF3 | pIK6.1MCVampac | 90 | 0/0 |
| pIKF3 | pIK6.1MCVampac | 90 | 0/0 |
| pRTD2.2ssaF3 | pIK6.1MCVampac | 78 | 33/35 |
| pRTD2.2svgF3 | pIK6.1MCVampac | 84 | 44/39 |
| pRTD2.2svgeF3 | pIK6.1MCVampac | 81 | 42/43 |
| pRTD2.2F15 | pIK6.1MCVampac | 93 | 70/70 |
| pRTD2.2F15 | pIK6.1MCVampac | 91 | 69/70 |

High titer virus can also be produced by cotransfection of pIK6.1amenvATG, pIK6.1gagpolATG and pRTD2.2F3 (Table 1). Although the transfection efficiency of the latter plasmids was approximately equal to the transfection efficiency of pIK6.1MCVampac and pRTD2.2F3, virus production was reduced by a factor of 2 to 27%. Similar results have been described by Landau and Litman (Landau and Litman, supra), where they observed a 5-fold decrease. The overall efficiency of the KAT system, using one or two genome packaging plasmids, is still 10 to 20-fold greater then that described for the COS cell system.

The high 3T3 cell transduction efficiency observed by FACS analysis of viral supernatants produced following KAT plasmid transfection of 293 cells was confirmed by Southern blotting of integrated proviral DNA from infected 3T3 cells. High molecular weight DNA was prepared 48 hours post infection and digestion of 10 µg of DNA with Eco RV. The samples were electrophoresed on a 0.8% agarose gel, transferred to Zetabind and probed with a 605 bp fragment encoding the zeta transmembrane and cytoplasmic domains. Eco RV digestion of the transfected plasmid pRTD2.2F3 yielded a 4.2 kb band. Eco RV digestion of pRTD1.2F3, which contains MMLV 5' and 3' LTRs, yielded a 3.6 kb fragment. Following virus infection, integration and duplication of the 3' LTR, Eco RV digestion should yield a 3.6 kb fragment. This allows determination of the presence of integrated proviral DNA in the target cells. Table 2 gives the sizes of the expected bands from transfected plasmid DNA and integrated provirus following Eco RV digestion and hybridization to the zeta probe.

TABLE 2

| Retroviral Construct | EcoRV Fragment Size (in Kb) Hybridizing to ζ Probe | |
|---|---|---|
| | Trasfected Plasmid | Integrated Provirus |
| pRT.D 2.2F3 | 4.20 | 3.60 |
| pRT.D 2.2SSAF3 | 3.80 | 3.20 |
| pRT.D 2.2SVGF3 | 4.17 | 3.57 |
| pRT.D 2.2SVGE-F3 | 4.22 | 3.61 |
| pRT.D 2.2F15 | 4.47 | 3.87 |

Figure 3A:
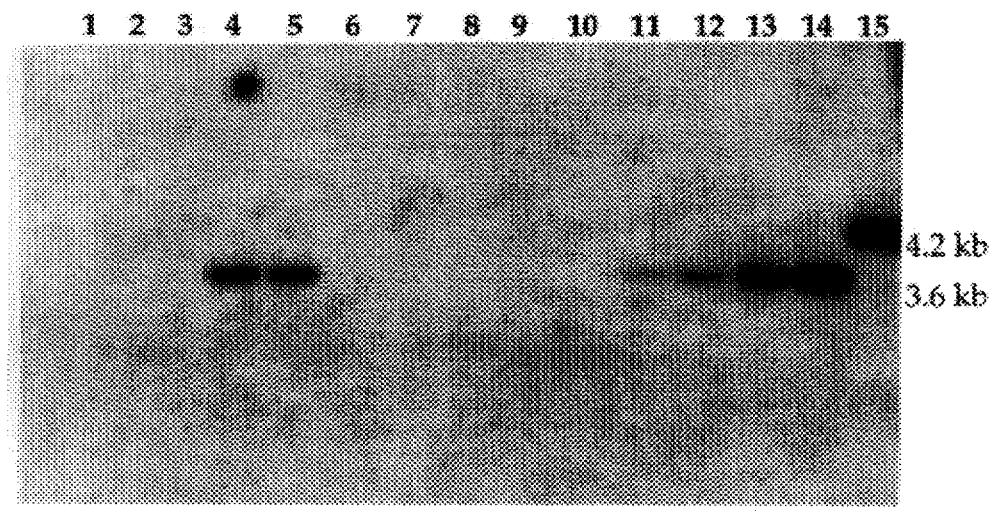
FIG. 3 (Parts A–B) shows the transduction efficiency determined by Southern blot analysis of infected 3T3 DNA, as described in Example I, infra.

Genomic DNA prepared from infected 3T3s was digested with Eco RV and 10 µg of digested DNA from infected and control cells were electrophoresed on a 0.8% agarose gel, transferred to Zetabind and probed with a 605 bp fragment encoding the ζ transmembrane and cytoplasmic domains. Only the DNA derived from 3T3 cells infected with supernatants obtained following cotransfection of 293 cells with pRTD2.2F3 and pIKMCVampac yielded a 3.6 kb fragment (FIG. 3A, lanes 4 and 5), identical to the fragment seen in the Eco RV digested pRTD1.2F3 plasmid control lanes (FIG. 3A, lanes 11–14), indicative of integrated provirus. Quantitation of southern blots by scanning densitometry and comparison to plasmid standards representing 0.1 to 3.0 copies, in 3-fold increasing increments (FIG. 3A, lanes 11–14), was consistent with a transduction efficiency of with a transduction efficiency of 0.5 copies/cell/ml of viral supernatant. The transduction efficiency was identical to the efficiency observed by FACS analysis. The probe did not detect a band in DNA from 3T3 cells infected with supernatants derived from mock transfected 293 cells (lane 1), 293 cells transfected with pRTD2.2F3 alone (FIG. 3A, lanes 2 and 3), transfected with the expression vector pIKF3 alone (FIG. 3A, lanes 6 and 7) or cotransfected with pIK6.1MCVampac and pIKF3 (FIG. 3A, lanes 8 and 9), which is also consistent with the FACS analysis.

Figure 3B:
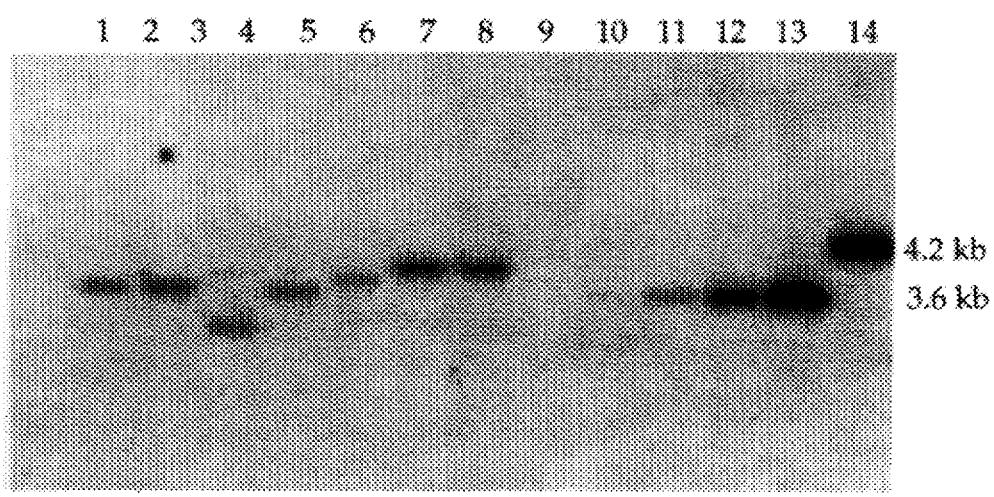

Three additional retroviral constructs, two which differed in the viral backbone, pRTD2.2SSAF3 (FIG. 3B, lane 4), pRTD2.2SVGF3 (FIG. 3B, lane 5), pRTD2.2SVGE-F3 (FIG. 3B, lane 6), and one which differed in the chimeric receptor insert, pRTD2.2F15 (FIG. 3B, lanes 7 and 8), were cotransfected into 293 cells with pIK6.1MCVampac, the supernatant used to infect 3T3 cells, followed by both FACS analysis (Table 1) and southern blotting (FIG. 3B). All of the F3 constructs showed similar titer by both FACS analysis (Table 1) and hybridized to the zeta probe with similar intensities, as expected. The F15 retrovirus had approximately 50% greater titer as determined by FACS analysis (Table 1), as well as by densitometric analysis of the Southern blots. Retrovirus as produced in 293 with each of the vectors, upon infection, yielded the correct size for the integrated provirus. Therefore, the FACS and Southern blotting results from 5 KAT retroviral constructs demonstrate that high titer retrovirus can be produced in 293 cells, that production was dependent upon cotransfection of the retroviral construct and packaging functions, and production of high titer retroviral supernatants in 293 cells does not lead to any unusual rearrangements of the retroviral constructs.

Virus Production in Mammalian Cell Lines

Seven additional cell lines were screened for their ability to produce retrovirus by cotransfection with KAT plasmids, followed by virus harvest and 3T3 infection (Table 3).

TABLE 3

| Cell Type | Packaging Construct | Surface CD4 % | 3T3 inf % | Retro-F3 Constr. |
|---|---|---|---|---|
| 293 | Mock | 1 | 0/0 | Mock |
| 293 | pIK6.1MCVampac | 88 | 39/38 | pRTD2.2-F3 |
| 293 | pIK6.1MCVampac | 88 | 41/38 | pRTD2.2-F3 |
| COS | Mock | 0 | ND | Mock |
| COS | pIK6.1MCVampac | 58 | 12/14. | pRTD2.2-F3 |
| COS | pIK6.1MCVampac | 58 | 14/15 | pRTD2.2-F3 |
| 143B | Mock | 0 | ND | Mock |
| 143B | pIK6.1MCVampac | 54 | 1/1. | pRTD2.2-F3 |
| 143B | pIK6.1MCVampac | 50 | 1/1. | pRTD2.2-F3 |
| HELA | Mock | 0 | ND | Mack |
| HELA | pIK6.1MCVampac | 48 | 0/0 | pRTD2.2-F3 |
| HELA | pIK6.1MCVampac | 54 | 0/0 | pRTD2.2-F3 |
| L929 | Mock | 0 | ND | Mock |
| L929 | pIK6.1MCVampac | 1 | 0/0 | pRTD2.2-F3 |
| L929 | pIK6.1MCVampac | 1 | 0/0 | pRTD2.2-F3 |
| 3T3 | Mock | 0 | 0/0 | Mock |

TABLE 3-continued

| Cell Type | Packaging Construct | Surface CD4 % | 3T3 inf % | Retro-F3 Constr. |
|---|---|---|---|---|
| 3T3 | pIK6.1MCVampac | 39 | 2/3. | pRTD2.2-F3 |
| 3T3 | pIK6.1MCVampac | 44 | 4/3. | pRTD2.2-F3 |
| CHO D— | pIK6.1MCVampac | 0 | 0/0 | pRTD2.2-F3 |
| CHO D— | pIK6.1MCVampac | 0 | 0/0 | pRTD2.2-F3 |

CD4 surface expression and virus production was absent from L929 and CHO D-following cotransfection of pIK6.1MCVampac with pRTD2.2F3. However, these cell lines were highly transfectable under conditions with a plasmid encoding the lac z gene was used. FACS analysis of transfected HELA, 143B, 3T3 and COS demonstrated high surface CD4 expression, with a transfection efficiency of approximately 50% for all four cell types. However, virus production among these cells was substantially different. HELA and 143B cells produced no virus at all, whereas 3T3 cells produced virus capable of 3% 3T3 transduction/ml of frozen supernatant. Cotransfection of COS cells with KAT plasmids, even in the absence of DNA replication of the retroviral construct, produced virus with titers of 4.5-fold greater than that produced by 3T3 cells. These titers, without plasmid replication of the viral vector construct, are 200 fold greater than those described by Landau and Litman (Landau and Litman, supra). This demonstrates that the KAT constructs are unique in their ability to produce retrovirus upon transfection of a wide variety of cells, without plasmid replication. Given the 100 fold increase that Landau and Litman observed with plasmid replication of the viral vector construct, transfection of KAT packaging function and retroviral vector plasmids that support plasmid replication, into hosts that support plasmid replication, could potentially further increase titer 10 to 100-fold and further increase the utility of KAT transfected cells to infect cell types that are currently difficult to infect.

EXAMPLE II

High Efficiency Transduction of Human T Cells

This example demonstrates the method of the invention in which 293 cells transfected with the KAT constructs are able to transduce primary, human target CD8+ T cells by cocultivation with high efficiency.

Construction of retroviral vectors and packaging plasmids

KAT constructs were prepared as described above in Example I.

Isolation and activation of human CD8+ T cells from peripheral blood

Primary human CD8+ T cells were purified from the peripheral blood of healthy donors as follows: Peripheral blood mononucleocytes (PBMCs) were isolated from human blood by Ficoll-Hypaque density gradient centrifugation. PBMCs were washed three times with D-PBSE/CMF (PBS containing 1mM EDTA, Ca and Mg free), resuspended at $5 \times 10^7$ cells in 4 ml of D-PBSE/CMF containing 0.5% of human gamma globulins, and incubated at room temperature for at least 15 minutes. After incubation, CD8+ T cells were purified from the PBMC cell suspension by positive panning. Specifically, the PBMC suspension was loaded into a pre-washed T-25 tissue culture flask coated with an antibody specific for the human CD8 receptor (AIS CD8 selection flask (Applied Immune Sciences, Santa Clara, Calif.)) at a density of $5 \times 10^7$ cells per 4 ml per T-25 flask. Cells were incubated for one hour at room temperature, and the non-adherent cells removed by gentle pipetting and washing the flask three times with the D-PBSE/CMF. The CD8+ T cells were simultaneously released from the flask and activated by adding 10 ml of T cell medium (see below for composition) containing 10 ng/ml OKT3 (Ortho Pharmaceuticals, Raritan, N.J.) and 10% IL2 (Pharmacia). Cells were incubated with this media for 48 hours, harvested from the flask, and washed once with T cell medium, and finally resuspended in fresh T cell medium plus 10% IL2 at a density of $0.5-1.0 \times 10^6$/ml in 24 well plates.

In order to remove residual cells (usually present at 2–3%) which cross-reacted with either the CD4-specific antibody used for detection of F3 surface expression, or the human Fc-specific antibody used to detect F15 surface expression, the enriched CD8+ T cell population was subjected to a further round of purification in which the contaminating cells were removed by negative panning, using AIS selection flasks described above, coated with either the anti-CD4 or anti-human Fc antibody. Specifically, the enriched CD8+ T cell population was incubated in the selection flask for one hour, and then non-adherent (i.e., highly purified CD8+ T cells) were removed. Cells were subsequently washed, and allowed to recover for 24 hours in the T cell medium plus 10% IL2 for 24 hours. CD8+ T cells prepared in this manner were greater than 95% CD8+ and CD3+, and less than 0.5% CD4+ or FC+, and were subsequently employed as targets for retroviral transduction.

Retroviral transduction of CD8+ T cells by cocultivation or supernatant infection 293 cells were plated at $1 \times 10^6$ cells/6 well plate, and then transfected with the appropriate construct after 48 hours as described above. 24 hours post transfection, the transfection media was removed and replaced with T cell growth media (see below for composition).

(a) Cocultivation: 2 to 4 hours later, $0.5 \times 10^6$ purified and activated human CD8+ T cells prepared as described above (usually at day 4 or 5 post-purification/activation) were added per well containing the transfected 293 cells, and polybrene added at a final concentration of 2 µg/ml. 24 hours after plating the 293 cells for the initial transfection, a second set of 293 cells were plated and transfected as described above. 24 hours after the initial cocultivation, T cells were removed from the first cocultivation and transferred to the second 293 transfection plate for an additional 24 hours of cocultivation employed the same conditions. Similar conditions were employed for transduction of CD8+ T cells by cocultivation with either transiently transfected 3T3 cells, or the stable PA317 producer cell line 40.39 (see below).

(b) Supernatant infection: $0.5 \times 10^6$ purified and activated human CD8+ T cells prepared as described above (usually at day 4 or 5 post-purification/activation) were incubated with 1 ml of fresh T cell medium (plus 10% IL2 and 2 µg/ml polybrene) together with 1 ml of viral supernatant obtained from the 293 transient transfection system described above, or from the stable PA317 producer cell line 40.39 (see below). After an 8 hour incubation period, 1.5 ml of medium was removed from each well, and replaced with 0.5 ml of fresh T cell medium together with 1.0 ml of viral supernatant (polybrene at 2 µg/ml and IL2 at 10%). After a 12 hour incubation period, the two step supernatant procedure was repeated.

For both cocultivation and supernatant infection, CD8+ T cells were allowed to recover for a 24–28 hour period in fresh T cell medium plus 10% IL2. Cells were then analyzed by flow cytometry for surface expression of either CD4 (for the CD4-ζ F3 receptor) or Fc for the F15 antibody-ζ receptor) in order to determine transduction efficiencies. T cells which were under cocultivation with transfected 293 cells were gently removed as a suspension from the 293 monolayer. Both cocultivated and supernatant infected T cells were washed 1× with phosphate buffered saline (PBS) plus 2% (FCS) fetal calf serum (Hyclone). T cells were then incubated with the appropriate FITC-conjugated detection antibody in the presence of PBS plus 2% FCS at a density of 1×10⁶/ml for 30 minutes at 40° C., washed 3× with PBS plus 2% FCS, and finally resuspended in 0.5 ml PBS and analyzed by flow cytometry.

The transduced CD8+ T cell population was subsequently maintained in T cell medium (10% FCS, Hyclone; RPMI1640, CellGro; 10 mM Hepes buffer (Gibco); 1% Sodium pyruvate (Gibco); 1% non-essential amino acids (Gibco); 2 mM glutamine (Gibco); 25 µM 2-mercaptoethanol (Sigma) and 1% streptomycin/penicillin). T cells were periodically re-stimulated every 7 to 10 days by the addition of OKT3 at 10 ng/ml or by exposing the cells to immobilized OKT3 in a T-25 tissue culture flask at a density of 1–2×10⁷ CD8+ T cells/10 ml T cell medium plus 10% IL2. Cells were incubated for 48 hours, washed 1× with T cell medium, and resuspended in fresh medium plus 10% IL2 at 0.5–1.0×10⁶/ml.

Analysis of CD8+ T cell Transduction

Transduction efficiency of primary human CD8+ T cells by retrovirus produced transiently using the KAT system was compared to retrovirus produced from a high-titer, stable producer clone derived from the amphotropic packaging line PA317 (Miller and Buttimore, supra). The stable producer clone 40.39, which transduces the F3 chimeric receptor was isolated by transfection of the ecotropic packaging line gpe (Markowitz et al. supra) with pRTD4.2F3, followed by supernatant harvest 48 hours post transfection and infection PA317 in the presence of 8 micrograms/ml of polybrene (Miller and Buttimore, supra). Individual clones were obtained by limiting dilution and 50 were screened for virus production by isolation of viral mRNA from the media of clones, followed by dot blot hybridization using a 603 bp zeta chain probe. The clone that gave the strongest hybridization signal, clone 40.39, was assayed by limiting dilution infection of 10⁶ NIH 3T3 cells followed by flow cytometry. 50 µl of supernatant transduced 17% cells, equivalent to 340% or an average of 3.4 proviral copies/cell/ml. The transduction efficiency following a 48 hour cocultivation with primary human CD8+ T cells with 40.39 producer cells was 1%–3% CD4+ (Table 4).

Figure 4:
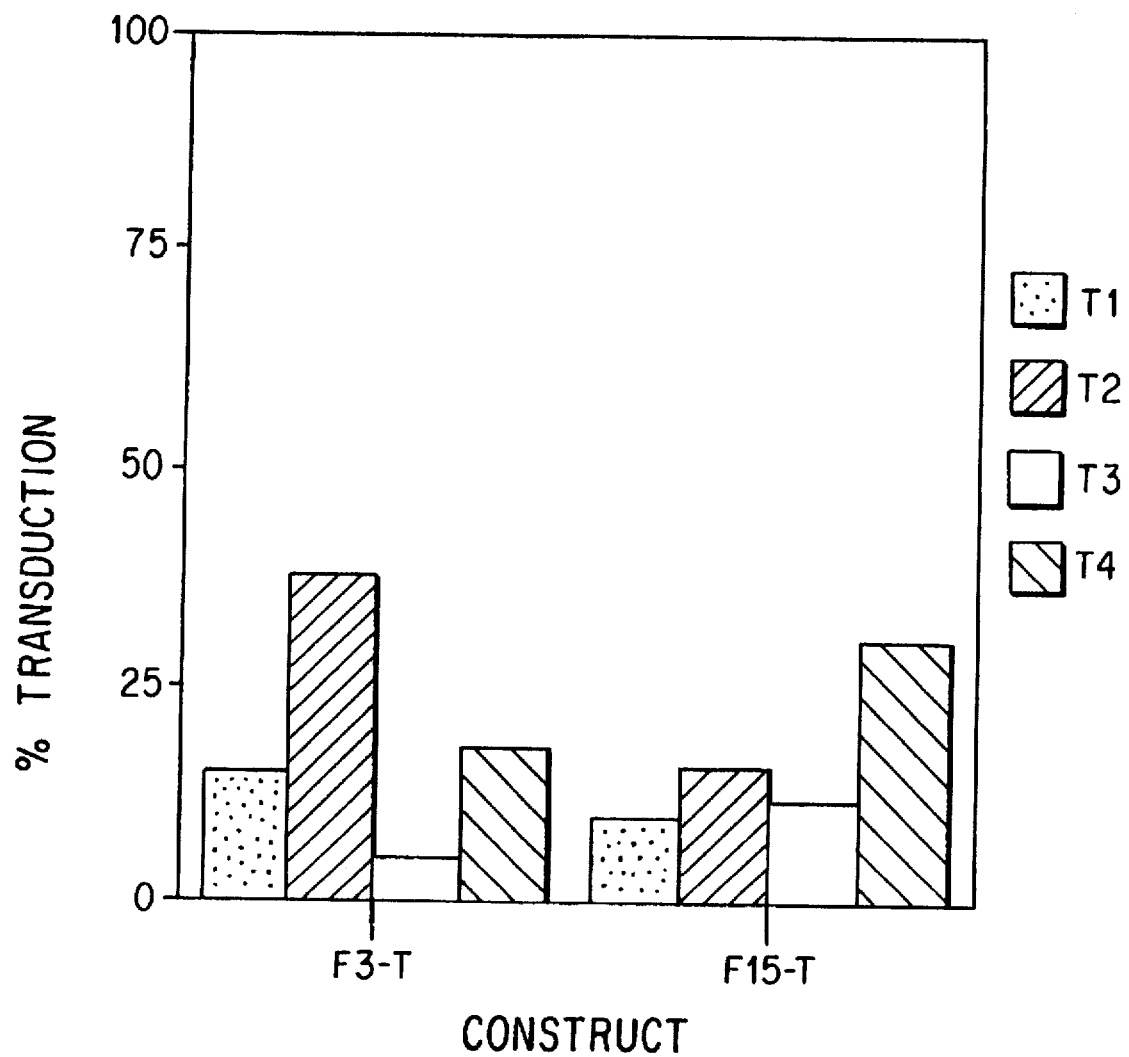
FIG. 4 is a bar graph of the data from experiments in which CD8+ T cells were transduced by, first, transient transfection of 293 cells with either pRTD2.2F3 or pRTD2.2F15 and pIK6.1MCVampac, followed by cocultivation of the 293 cells with the CD8+ T cells and analysis of transduction efficiency by FACS, as described in Example II, infra.
Figure 5B:
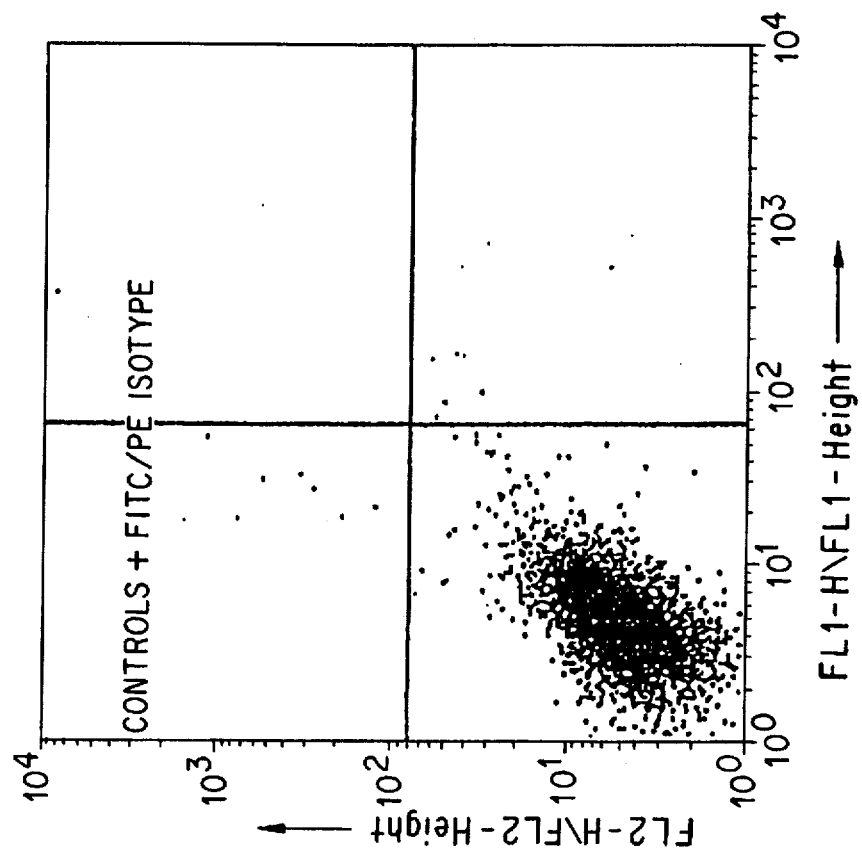
FIG. 5 (Parts A–D) shows the results of FACs analysis of hematopoietic stem cells transduced with the KAT packaging constructs and cocultivation with 293 cells, as described in Example III, infra.
Figure 5A:
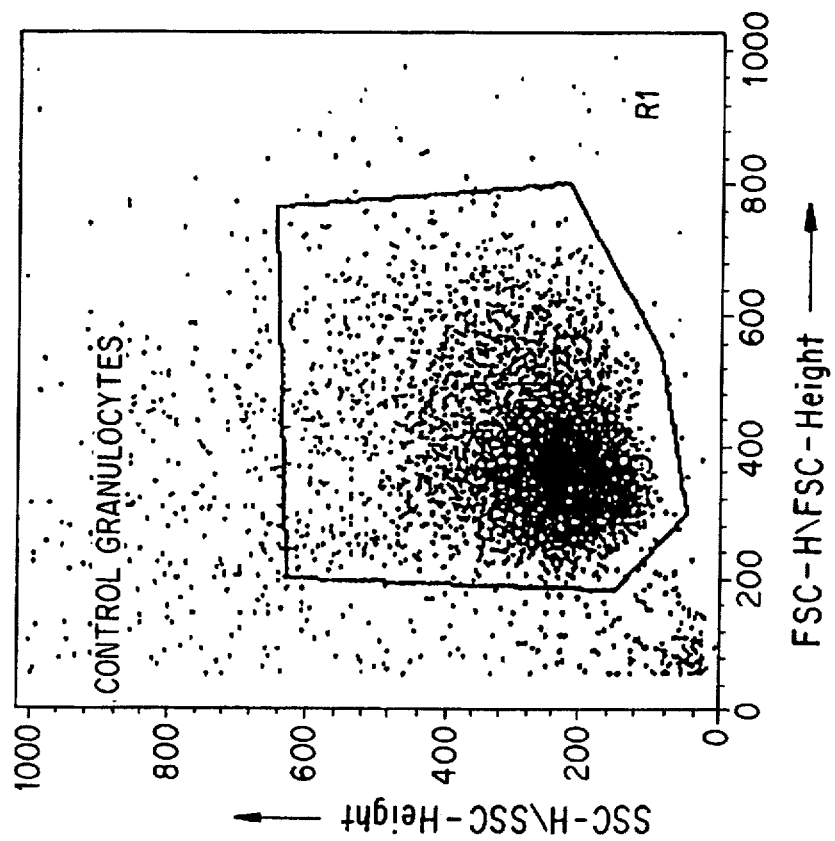
Figure 5D:
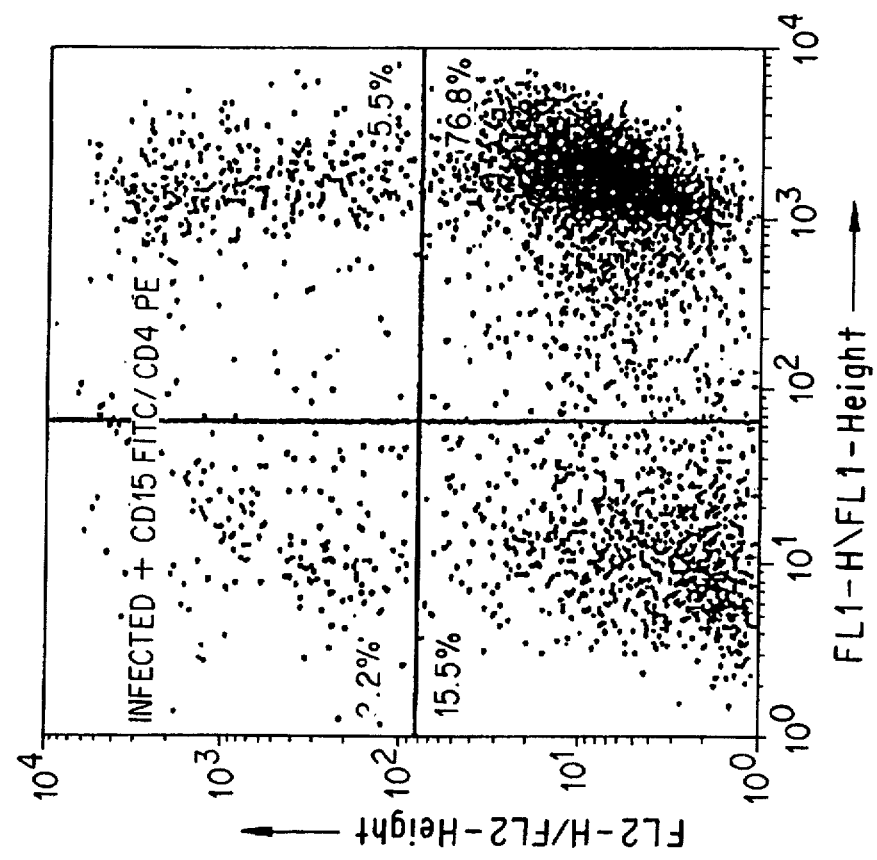
Figure 5C:
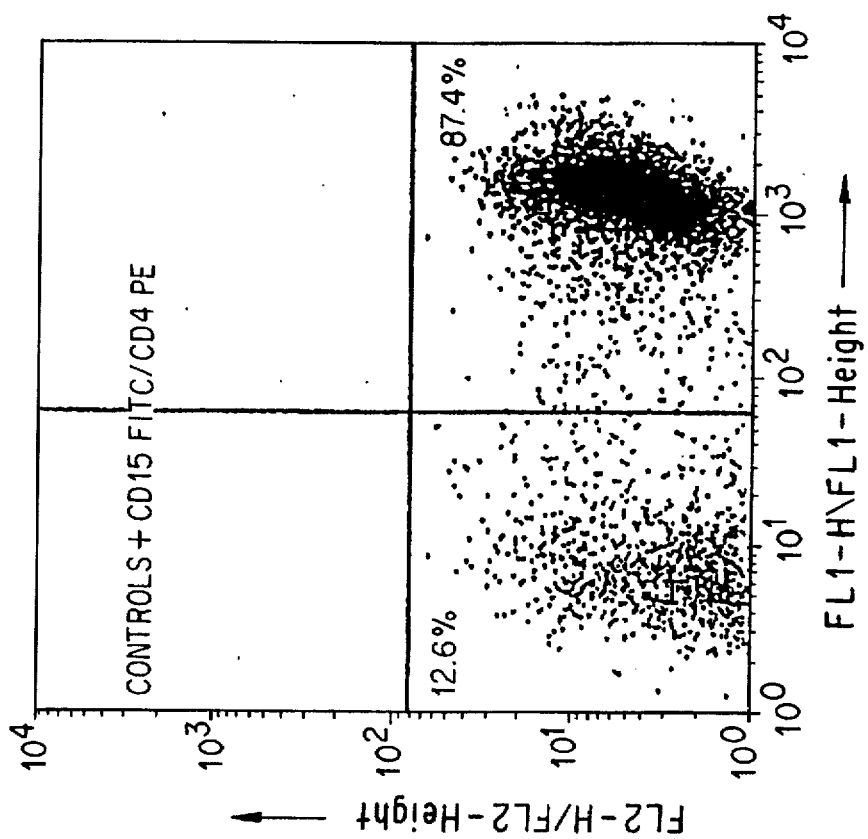

This result was compared to the transduction efficiency following the KAT transient-transfection and cocultivation method of the invention, which was used to transduce the chimeric receptor F3 and F15 into CD8+ T cells (FIG. 4). Four experiments were carried out in which CD8+ T cells were cocultivated on transfected 293 cells for 48 hours, followed by harvest and growth of T cells for 14 days and analysis of transduction efficiency by FACS as described above. The transduction efficiency of CD8 cells with both F3 and F15 constructs varies between 8% and 38%, and appears to be highly donor dependent. However, on average, this efficiency is 8 to 12-fold greater than the transduction efficiency obtained by cocultivation with the high-titer stable PA317 clones tested. In addition, the high transduction efficiency is not specific to F3 constructs because F15 constructs are transduced at similar efficiencies (FIG. 4). This data demonstrates that CD8 T cells can be transduced at efficiencies that are at least 5 fold greater than or equal to any other published reports, and that generation of stable producers are not required.

Supernatants from transduced T cells, 3 weeks post-transduction, were tested in an extended S+L-assay (Miller et al., Mol. Cell. Biol. 5:431–437 (1985)) and shown to be free of replication-competent retrovirus.

High efficiency transduction is mediated by cell-cell contact

In order to explore the mechanism of the high efficiency CD8 T cell transduction following transient transfection of KAT plasmids and cocultivation with CD8+ T cells, the transduction efficiency of CD8+ T cells using the following approaches was compared: (1) infection with supernatants derived from a high titer, stable PA317 producer line, (2) cocultivation with a high titer, stable PA317 producer line (3) infection with supernatants derived from transient transfection of NIH 3T3 cells with pIK6.1MMSVampac and pRTD4.2F3 (4) 48 hour cocultivation with NIH 3T3 cells following transient transfection with pIK6.1MMSVampac and pRTD4.2F3 (5) infection with supernatants derived from transient transfection of 293 cells with pIK6.1MCVampac and pRTD2.2F3 and (6) 48 hour cocultivation with 293 cells following transient transfection with pIK6.1MCVampac and pRTD2.2F3 (Table 4). For each transient transfection experiment, duplicate plates of transfected cells were used to harvest media for supernatant infection of 3T3 cells and duplicate plates were used for cocultivation of CD8 T cells. The same approach was used for stable producers.

TABLE 4

| Expt. # | Pkg. Line | Virus Production Method | Infection Method | 3T3 titer Supernatant | % T-cell Transduction |
|---|---|---|---|---|---|
| 1A | PA317 | PA317, Stable | Supernatant | 70% | 1 |
| 1B | PA317 | PA317, Stable | co-cultivation | ND¹ | 3 |
| 1C | 3T3 | KAT, Transient | co-cultivation | 26% | 3 |
| 1D | 293 | KAT, Transient | co-cultivation | 14% | 10 |
| 2A | PA317 | PA317, Stable | Supernatant | 30% | 1 |
| 2B | PA317 | PA317, Stable | co-cultivation | 30% | 1 |
| 2C | 293 | KAT, Transient | Supernatant | 45% | 1 |
| 2D | 293 | KAT, Transient | co-cultivation | 45% | 14 |

ND¹ = not determined

Supernatant infection of CD8+ T cells was 1%, whether the virus was produced in 293 cells, 3T3 cells or a stable PA317 producer (Table 4, experiments 1A, 2A and 2C). In contrast, cocultivation of CD8 T cells with 293 cells cotransfected with pIK6.1MCVampac and pRTD2.2F3, resulted in 10% to 14% CD8 T cell transduction (Table 4, experiment 1D, 2D). 10 to 14-fold greater than all supernatant infections, including supernatants produced by cotransfection of these plasmids into 293 cells. This demonstrates that cell-cell contact is responsible for high efficiency transduction of CD8+ T cells. In addition, the efficiency of KAT transfection followed by cocultivation is 1 to 3-fold greater than the transduction efficiency of cocultivation with a stable PA317 producer when 3T3 cells are used (compare 1B and 2B with 1C, table 4) and 5–10 fold greater when 293 cells are used. This data confirms that 293 cells have unique properties that support high efficiency transduction of mammalian cells.

While not wishing to be limited to any particular theory of the invention, these results suggest that high titer virus production into the culture media is not sufficient for efficient T cell transduction and that the high efficiency transduction observed is mediated by cell-cell contact of 293 cells and CD8+ T cells, resulting in up to ten-fold greater efficiencies.

The results presented in this example demonstrate that, in the absence of selection, 10–40% of the CD8+ T cells were virally transduced, a significantly greater transduction frequency compared to prior results.

EXAMPLE III

Transduction of Primary Human Hematopoietic Stem Cells

This example describes the use of the KAT constructs and method of the invention to transduce primary human CD34+ bone marrow stem cells.

Preparation of Bone Marrow Cells

Human bone marrow was obtained from healthy volunteers. It was first fractionated into a mononuclear cell fraction over a Ficoll gradient (Pharmacia, Piscataway, N.J.). The CD34+ cells are isolated using positive selection on a CellPro CEPTRATE LC™ affinity column (CellPro, Bothell, Wash.). Post-purification FACS analysis provided a population of approximately 90% CD34+ cells. This population of cells was then plated in 24 well plates at a density of $5 \times 10^5$ cells/ml in Myeloid Long Term Culture Medium supplied as a complete medium from Terry Fox Labs, (Vancouver, Canada) in the presence of 100 ng/ml human Stem Cell Factor (hSCF) (R&D Systems, Minneapolis, Minn.) 50 ng/ml hIL-3, and 10 ng/ml hIL-6 for 48 hours.

Transduction of CD34+ bone marrow stem cells 293 cells were transfected by first plating at a density of $1 \times 10^6$ cells/6 well plate 48 hours prior to transfection, followed by transfection with 10 µg each of pRTD2.2F3 and pIK6.1MCVampac. Twenty-four hours later, transfection media was removed, replaced with T cell growth media, as described in Example II, plus 50 ng/ml hIL-3, 100 ng/ml hSCF, and 10 ng/ml hIL-6. Two to four hours later, the transfected 293 cells were cocultivated with $5 \times 10^5$ purified CD34+ cells/well in the presence of 8 µg/ml polybrene. After 48 hours, the cells were collected off of the 293 monolayer, and replated in Myeloid Long Term Media with growth factors as described above. Cultures were replenished with media plus growth factors daily via demi-depopulation. Four days later, the media was replenished and G-CSF was added at 2 ng/ml plus 20 ng/ml hSCF to promote differentiation into granulocytes. Four to six days later, cells were analyzed for surface expression of human CD4 from the transduced gene and CD15, a granulocyte marker. In addition, DNA was prepared for Southern blot analysis.

FIG. 5 shows the FACS analysis of the transduced hematopoietic stem/progenitor cells after 14 days of growth and differentiation into granulocytes. Panel A shows the forward and side scatter gates used in the analysis of all cell populations in the FIGURE. In panel B are shown the untransduced cells stained with the isotype control antibodies (FITC and PE). In panel C are shown the untransduced cells stained with antibodies for human CD4 (transduced gene, y axis) and CD15 (granulocyte differentiation marker, x axis). In panel D, KAT packaging system was used in conjunction with 293 cell co-cultivation to transduce the hematopoietic stem/progenitor cells. A comparison of the top right quadrant for panels C and D indicate that 5–6% of the transduced cells expressed the CD4 protein.

Southern blot analysis of transduction efficiency

Figure 6:
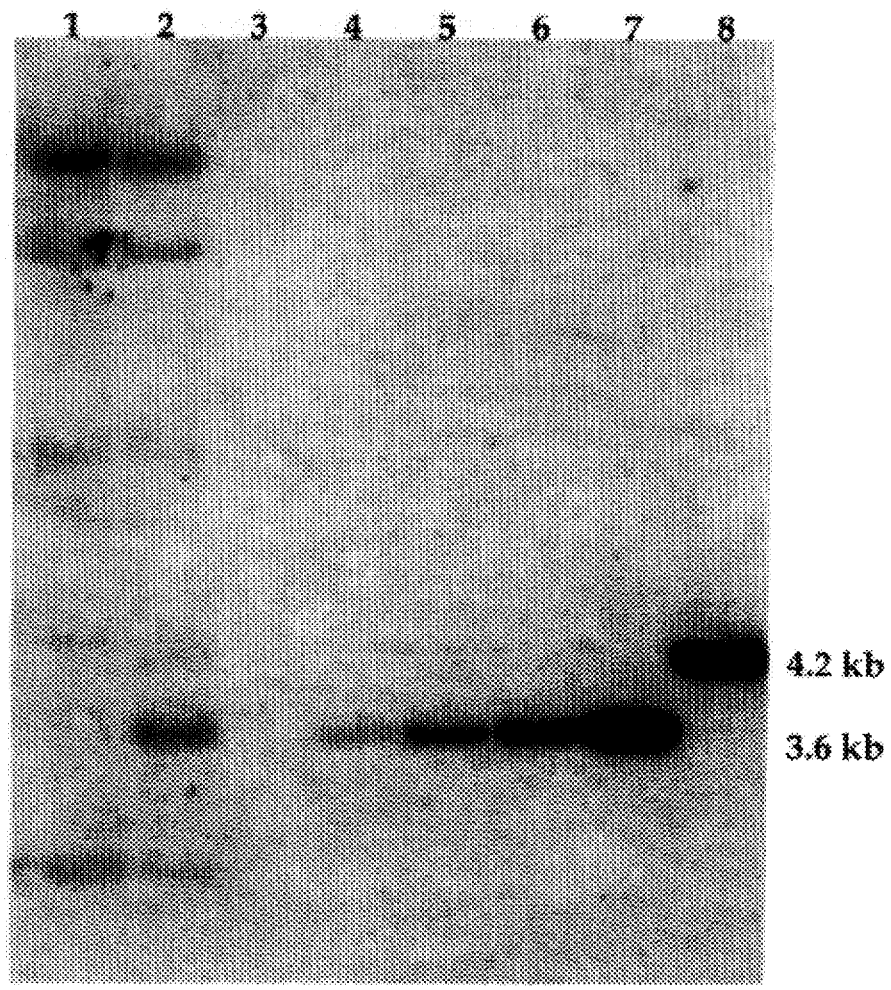
FIG. 6 examines whether the cocultivation of CD34+ cells with KAT transfected 293 cells leads to high efficiency transduction as analyzed by Southern blotting, as described in Example III, infra.

Southern blot analysis was carried out to determine whether the hematopoietic stem/progenitor cells were infected by retrovirus produced with the KAT system. Genomic DNA was prepared from differentiated stem cells and digested with Eco RV. 10 µg of DNA from infected (FIG. 6, lane 2) and control cells (FIG. 6, lane 1), as well as Eco RV-digested plasmid DNA equivalent to 0.12, 0.6, 1.2 and 6.0 copies per diploid genome of pRTD1.2F3 (FIG. 6, lanes 4–7) and 5 copies per diploid genome of pRTD2.2F3 (FIG. 6, lane 8) were electrophoresed on a 0.8% agarose gel, transferred to Zetabind and probed with a 605 bp fragment encoding the zeta transmembrane and cytoplasmic domains. Eco RV digestion of the transfected plasmid pRTD2.2 yields a 4.2 kb band (FIG. 6, lane 8). Eco RV digestion of pRTD1.2, which contains MMLV 5' and 3' LTRs, yields a 3.6 kb fragment (FIG. 6, lanes 4–7). Following virus infection, integration and duplication of the 3' LTR, Eco RV digestion should yield a 3.6 kb fragment. In infected CD34+ cells, the probe hybridized to the appropriate 3.6 kb band, corresponding to integrated provirus (FIG. 6, lane 7). Control cells lacked a proviral band, however the probe hybridized to bands that corresponded to the endogenous zeta gene sequences (FIG. 6, lane 8). Scanning densitometry was used to quantitate transduction efficiency and demonstrated that the average proviral copy number per cell in infected cells was 0.5 (50% transduction). In addition, densitometry of the endogenous bands confirmed that equal amounts of DNA were loaded in the lanes corresponding to infected and uninfected cells.

Figure 7:
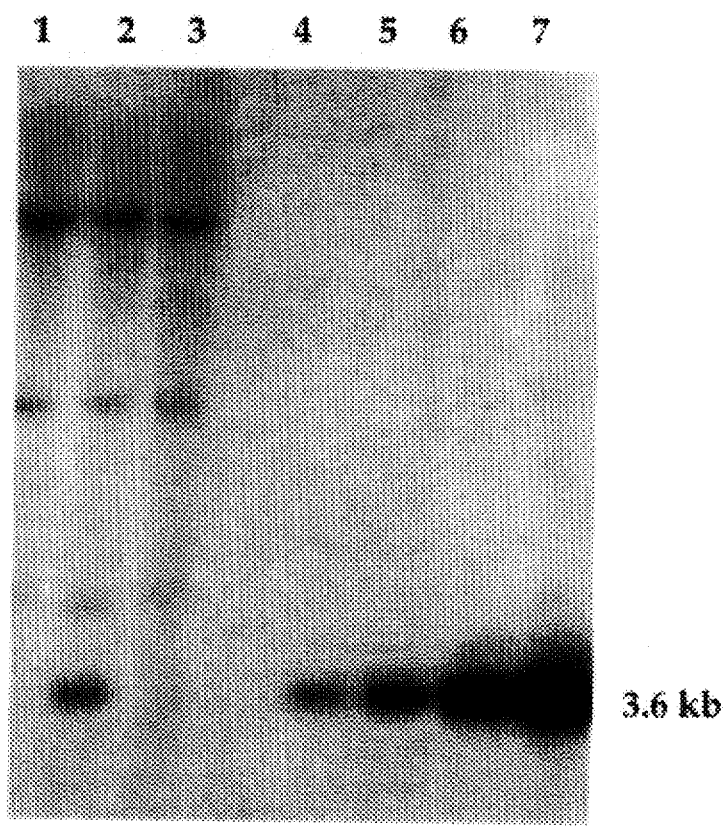
FIG. 7 compares the transduction efficiency of CD34+ cells transduced by the KAT system to that of cocultivation with a stable PA317 producer by Southern blotting, as described in Example III, infra.

In a second experiment, the transduction efficiency of a high titer PA317 producer clone was compared to the transduction efficiency of virus produced by the KAT system. 293 cells were transient cotransfection with pIK6.1MCVampac and pRTD2.2F3,isolation of CD34+ cells, cocultivation, purification of infected cells was carried out as described above. Clone 40.39, described above in Example II, was plated at $5 \times 10^5$ cells/6 well plate 24 hours prior to initiation of cocultivation with CD34+ cells. Isolation of CD34+ cells, cocultivation, purification of infected cells was carried out as described for 293 cells. Transduction efficiency was analyzed by southern blotting of Eco RV digested DNA as described above and is shown in FIG. 7. The band present in DNA isolated from CD34+ cells cocultivated with KAT plasmids hybridized to a 3.6 kb band (FIG. 7, lane 2), identical in size to Eco RV digested plasmid DNA (FIG. 7, lanes 4–7) and corresponding to integrated provirus. Hybridizing bands were absent from DNA isolated from CD34+ cells cocultivated with either mock transfected 293 (FIG. 7, lane 1) cells or 40.39 cells (FIG. 7, lane 3). The plasmid standards ranged from 0.3 to 10 copies of integrated provirus per cell. Therefore, the absence of a band in the PA317 lane suggests that KAT transduction is at least 10-fold more efficient.

Although FACS analysis of surface expression of the transduced gene indicates only a 5–6% efficiency of transduction, Southern analysis indicates a much higher efficiency of transduction (50–100%). It is possible that the level of expression of the human CD4 protein is below the level of detection of the FACS analysis, alternatively, the gene may be present but not efficiently expressed. Modifications to the constructs could be made to increase the level of expression. The high efficiency of transduction of human hematopoietic stem/progenitor cells via the KAT packaging system in conjunction with 293 cell co-cultivation is contrasted to the transduction efficiencies obtained using traditional mouse fibroblast packaging systems such as PA317. FIG. 7. The data from the PA317 packaging line indicates that although high titer virus can be generated when transducing mouse cells, the transduction efficiency of human bone marrow stem/progenitor cells is poor.

These results demonstrate, that, in addition to rapid production of high titer viral supernatants, the KAT constructs can be used to transduce at high efficiencies target cells, such as human T cells and hematopoietic cells, that are refractory to transduction by conventional methods.

EXAMPLE IV

Production of High Titer Virus in Human Cells with pIKT Retroviral Vectors and High Efficiency Transduction of Human CD34+ Hematopoietic Cells This example describes the use of the novel retroviral vectors of the invention to obtain high titer virus in a human cell line and the use of that virus to obtain high efficiency transduction in primary human hematopoeitic stem cells.

The packaging vector pIK6.1MCVampac UTΔ described above and the retroviral vector pIKT2.2SVGe-F3 were transiently co-transfected (as described above) into human tsa54 cells as described above. tsa54 cells were derived from 293 cells by the transfection of the Large SV40 T antigen (Heinzel et al., *J. of Virol.* 62(10):3738–3746 (1988)). pIKT2.2SVGe-F3 differs from pRTD2.2F3 in that the plasmid backbond contains the SV40 origin of replication as described above. This results in high copy number plasmid replication in tsa54 cells containing the SV40 t-antigen. tsa54 cells were transfected, viral supernatants were harvested and used to infect 3T3 cells as described above. 38% CD4 positive cells/100 µl frozen viral supernatant equivalent to 7×10⁶/ml.

The pIKT vectors were used to produce retrovirus in tsa54 cells as described above and used to transduce primary human CD34+ bone marrow stem cells by co-cultivation. The bone marrow stem cells were purified and transduced with the pIKT2.2SVGe-F3 as described above in Example III with the following changes. tsa54 cells were transfected at a density of 5×10⁵ cells/6 well plate. The media used to replace the transfection media was IMDM+10% FBS (fetal bovine serum). CD34+ cells were removed following two days co-cultivation with virus-producing tsa54 cells and cultured in Meloid Long Term Media with growth factors. Eight to ten days later G-CSF was added at 2 ng/ml plus 10 ng/ml hSCF to promote differentiation. Cells were analyzed for surface expression of human CD4 six to eight days later.

Figures 8A, 8B, 8C:
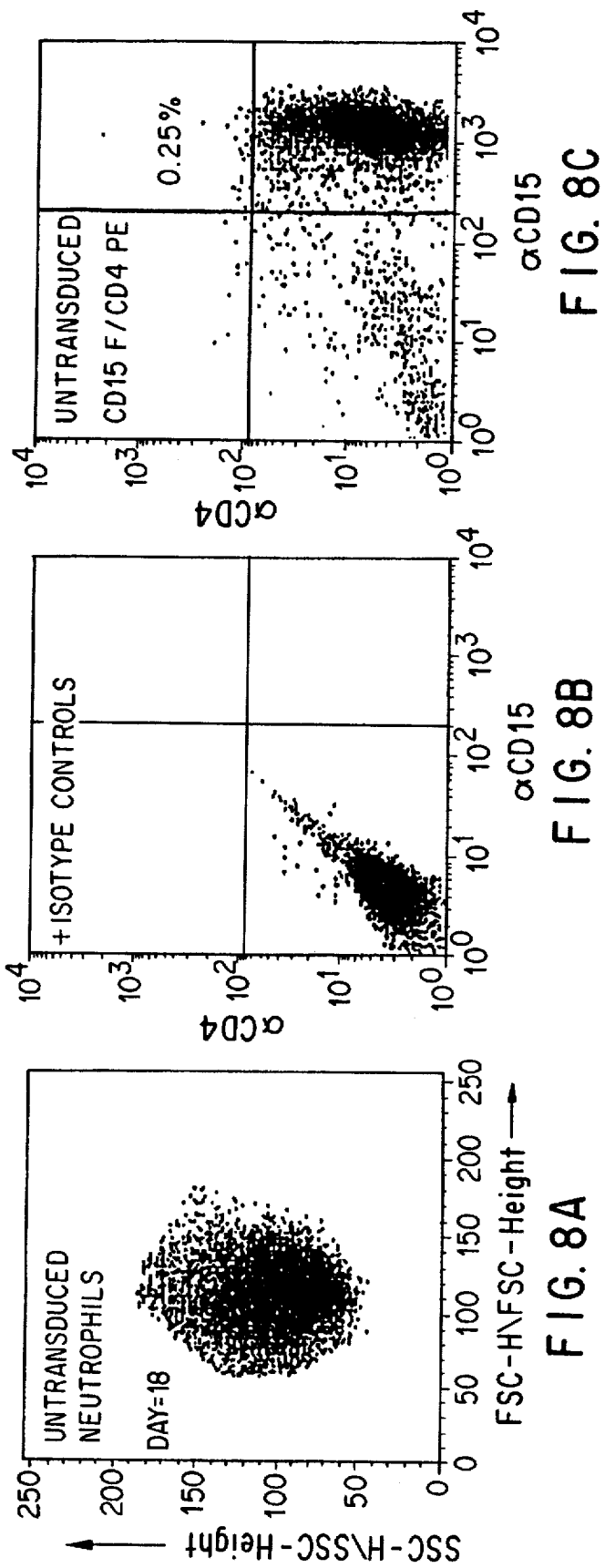
FIG. 8 (parts A–E) shows the results of FACs analysis of human CD34+ hematopoietic progenitors transduced with the KAT pIKT retrovirus vector constructs following transfection of 293 cells with pIKT vectors and cocultivation, as described in Example IV, infra.
Figure 8E:
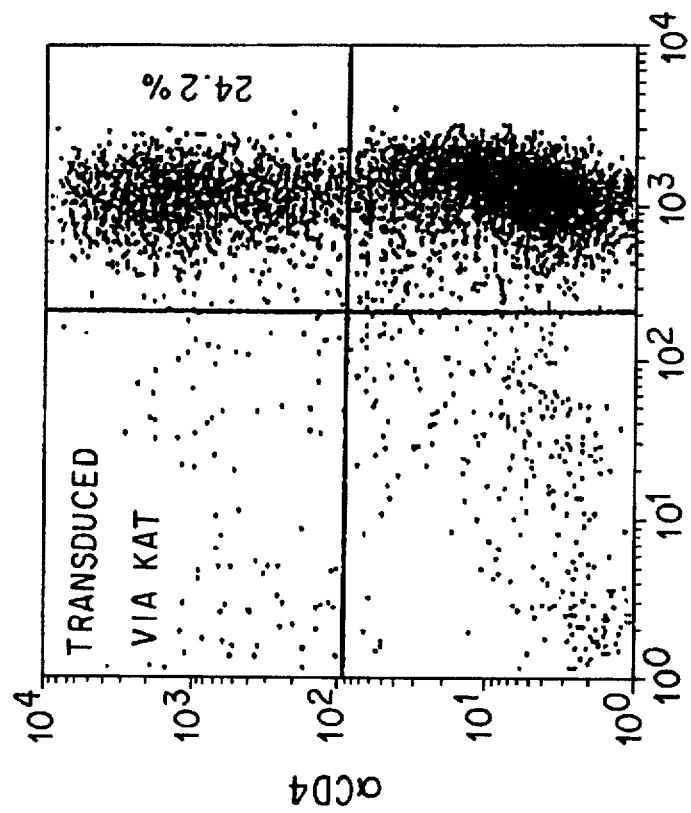
Figure 8D:
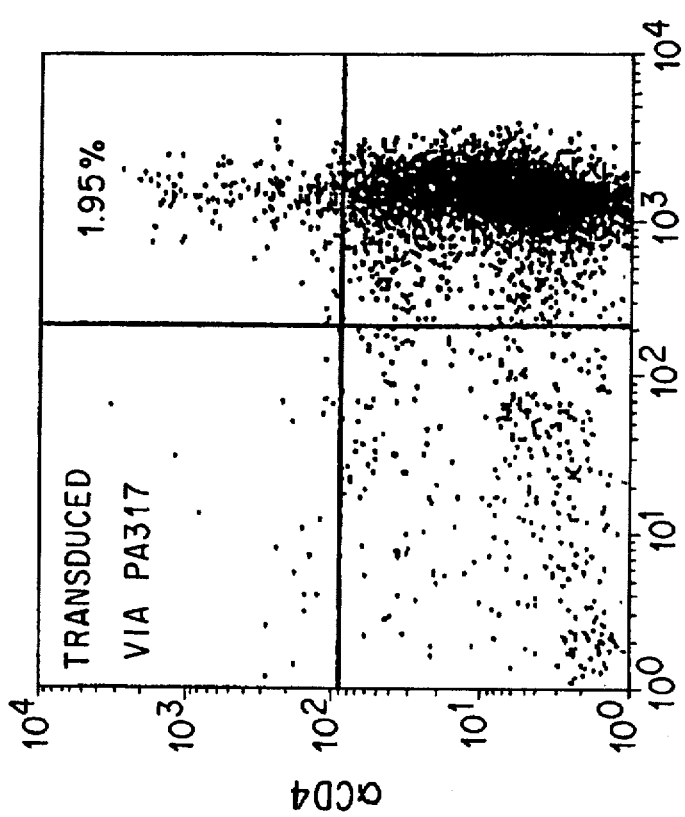

FIG. 8 shows the results of FACS analysis of the transduced hematopoietic stem/progenitor cells after 18 days of growth and differentiation into granulocytes. Panel A shows the forward and side scatter gates used in the analysis of all cell populations in the FIGURE. In panel B are shown the untransduced cells stained with the isotype control antibodies (FITC and PE). In panel C are shown the untransduced cells stained with antibodies for human CD4 (transduced gene, y axis) and CD15 (granulocyte differentiation marker, x axis). In panel D a PA317 clone (78.81), with a titer equivalent to 10⁷ neor CFU clones/ml on 3T3 plates, was used as a stable viral producer in a co-cultivation with the hematopoietic stem cells. In panel E, KAT packaging retroviral vectors were used in conjunction with 293 cell co-cultivation to transduce the hematopoietic stem/progenitor cells. A comparison of the top right quadrant for panels C and D, and C and E indicates that 1.7% of the PA317 transduced cells expressed the CD4 protein as compared to 24% of those transduced using the KAT constructs.

EXAMPLE V

Production of a Single Vector 293 or tsa54 Stable Packaging clone

This example describes the production and use of a single vector packaging clone. Human 293 or tsa54 cells were plated at 5×10⁵ per 10 cm plate in DME (JRH Biosciences, Lenexa, Kans.), 1 g/l glucose, 10% Donor calf serum (Tissue Culture Biologics, Tulare, Calif.) 48 hours prior to transfection. 10 µg MCV ampac UTΔ and 0.1 µg MC1 neo (Thomas and Capecchi *Cell* 51:503–512 (1987)) were cotransfected by calcium phosphate precipitation (Wigler et al. *Cell* 16:777 (1979)). Clones could were also generated as efficiently by co-electroporation of the vectors (Shigekawa and Dower *Biotechniques* 6(8):742–751 (1988)). 18 hours post-transfection the media was changed. 24 hrs. later the cells were split to duplicate plates of 1:10, 1:20 and 1:50 in media plus 1 mg/ml G418 (Geneticin, GIBCO, Grand Island, N.Y.). Media was changed every 3 days for 14 days. Clones were picked to 24 well plates and grown to confluence. Media was collected from wells, filtered through a 0.45 µm filter and flash frozen on dry ice. Cells were resuspended in media plus 10% DMSO (Sigma Chemical Co., St. Louis, Mo.), frozen on dry ice and stored at –70° C. Supernatants were assayed for production of empty viral particles using an assay for reverse transcriptase which measures the incorporation of radiolabeled thymidine into an RNA template. (Goff et al. *J. of Virol.* 38:239–248 (1981)).

Clones with the strongest reverse transcriptase signals following autoradiography were thawed, grown up and tested for virus production following transient transfection. Transfections were done as previously described, using 10 µg 43.3PGKF3. Media was changed 18 hours post-transfection. After 24 hours the viral supernatants were collected, filtered through 0.45 µm filters and flash frozen on dry ice. Viral supernatants were assayed on 3T3 cells plated at 5×10⁵ per 10 cm plate 24 hours prior to infection. Infections were done as described above. Cells were then harvested, stained with OKT4A anti-CD4 monoclonal antibody (Ortho Diagnostic Systems Inc., Raritan, N.J.), and analyzed by flow cytometry as described above. Clones displayed varying amounts of packaging function. Those clones with the highest transient titer were selected for further characterization (Table 5).

TABLE 5

| CELLS/CLONE # | VECTORS | Transduction Efficiency (% CD4 + 3T3 Cells) |
|---|---|---|
| tsa54 | none | 1.02 |
| tsa54/107.14 | ampac + 43.2 | 2.53 |
| tsa54/107.17 | ampac + 43.2 | 0.67 |
| tsa54/107.18 | ampac + 43.2 | 29.76 |
| tsa54/107.22 | ampac + 43.2 | 1.76 |
| tsa54/107.24 | ampac + 43.2 | 6.47 |
| tsa54/107.25 | ampac + 43.2 | 0.61 |
| tsa54/107.26 | ampac + 43.2 | 1.70 |
| tsa54/107.49 | ampac + 43.2 | 0.89 |
| tsa54/107.57 | ampac + 43.2 | 1.12 |
| tsa54/107.73 | ampac + 43.2 | 1.33 |
| tsa54/107.75 | ampac + 43.2 | 13.18 |
| tsa54/107.142 | ampac + 43.2 | 0.98 |
| 293/90.74 | ampac + 43.2 | 24.80 |
| 293/90.85 | ampac + 43.2 | 15.06 |

Clones 90.74, 107.75, and 107.18 were carried for extended time in culture to study ability to maintain the packaging genome over time in the presence or absence of G418. Cells were split 1:10 to 1:20 every 3 to 4 days. At passages 1, 6 and 12 cells were transfected with 10 µg 43.2 as described above, and transient viral supernatants were analyzed by infection of 3T3 cells as described above. Of the three clones studied, only one (90.74) appeared to have consistent titer over 12 passages (Table 6). It also appeared that titer did not depend on continued G418 selection. Clone 90.74 has a transient titer equivalent to approximately 10⁷/ml. Clone 90.74 has been deposited with the ATCC, 12301 Parklawn Drive, Rockville, Md., under the Budapest Treaty, and has there been identified as follows:

| Cell Line | ATCC Accession No. | Deposit Date |
|---|---|---|
| 90.74 | | June 10, 1994 |

TABLE 6 tsa AMPAC STABILITY TEST
Transduction Efficiency
(% CD4 + 3T3 Cells/0.25 ml supernatant)

| CLONE | VECTORS | p1 | p6 | p12 |
|---|---|---|---|---|
| tsa | none | 0.10 | | 1.20 |
| tsa | Ampac | 0.10 | | 4.06 |
| tsa | Ampac + 43.2 | 63.90 | 30.97 | 66.94 |
| 107.18 + G418 | Ampac + 43.2 | 41.50 | 22.35 | 22.68 |
| 107.18 | Ampac + 43.2 | — | 23.50 | 26.22 |
| 107.75 + G418 | Ampac + 43.2 | 15.42 | 12.18 | 4.36 |
| 107.75 | Ampac + 43.2 | — | 11.17 | 2.05 |
| 90.74 + G418 | Ampac + 43.2 | 34.83 | 30.79 | 27.79 |
| 90.74 | Ampac + 43.2 | — | 28.40 | 31.32 |

Supernatants were also analyzed for production of RCR by a S+/L-assay on PG4 cells. PG4 cells are Moloney sarcoma virus-transformed cells from cat brain (ATCC CRL2032). When infected with competent murine retrovirus, PG4 cells produce discernable foci which can be distinguished microscopically (Haapala, et al. *J. of Virol.*, 53(3):827–833). PG4 cells were seeded at 5×10⁶ on 10 cm plates 24 hours prior to infection. Infections were done with 1 ml of test supernatant and 4 mls of media containing 8 μg/ml polybrene. Media was changed 24 hours later, and then replaced every 2–3 days until foci developed on positive control plates. All clones studied remained RCR-free through 12 passages.

Unexpectedly, these results demonstrate that using the retroviral vectors of the invention, stably transfected 293-derived cell lines that produce gag, pol and env proteins were generated. The virus production from these cell lines was equivalent to that produced from transient co-transfection of packaging and retrovirus vectors. Moreover, surprisingly, in the absence of drug selection, these cell lines maintained production of gag, pol and env proteins. Previous attempts to generate 293-based retroviral producers using retrovirus constructs described in the literature have failed (Pear et al. *Proc. Nat'l Acad. Sci. (USA)* 90:8392–8396 (1993)). After extended passage in culture these packaging cell lines do not spontaneously generate replication competent retrovirus.

EXAMPLE VI

Production of Double Genome Stable Packaging Cells

This example describes the construction and use of two genomes in 293 or tsA54 packaging cells. First a gag/pol clone was created in human tsa54 cells. Cells at 1×10⁶ per 0.8 ml of PBS were co-electroporated with 15 μg NotI linearized gag/pol ATG (described above) and 1 μg MC1 neo. Electroporation was done at 960 μF and 260 mV (Shigekawa and Dower, (1988) supra) on a Gene Pulser (Biorad, Richmond, Calif.). Cells were immediately plated on a 10 cm plate in DME, 1 g/l glucose, 10% donor calf serum for 48 hours. Cells were then split 1:5, 1:10, 1:20 and 1:50 in 1.0 mg/ml G418 selection. Media was changed every 3 days, and after 12 days of selection in G418 clones were picked to 24 well plates. Once cells were confluent, media was collected, filtered through a 0.45 μm filter and flash frozen on dry ice. Clones were trypsinized and frozen at −70° C. Supernatant was thawed and analyzed for reverse transcriptase activity (Goff et al., (1981) supra). Those clones displaying the highest RT activity were grown up and evaluated for transient virus production by calcium phosphate transfection of 5 μg pIK6.1MCVamenvATGUTΔ described above and 10 μg pRT43.2F3 described above. Media was changed after 18 hours, and after an additional 24 hours the viral supernatants were collected, filtered and frozen for analysis by infection of 3T38. Transient virus titers were comparable to the transient virus titer of the single genome pack line 90.74 transfected with pRT43.2F3, and approximately 50% of the viral titer following co-transfection of tsA54 cells with pIK6.1MCVampacUTΔ and pRT43.2F3 (Table 7).

TABLE 7

GAG/POL TRANSIENT TEST

| CLONE | VECTORS | Transduction Efficiency (% CD4 + 3T3 Cells) |
|---|---|---|
| tsa | | 0.02 |
| 293/90.74 | ampac + 43.2 | 28.50 |
| tsa54/111.3 | gag/pol + 43.2 | 11.72 |
| tsa54/111.8 | gag/pol + 43.2 | 13.30 |
| tsa54/111.44 | gag/pol + 43.2 | 20.29 |
| tsa54/111.89 | gag/pol + 43.2 | 17.93 |
| tsa54/111.4 | gag/pol + 43.2 | 32.95 |
| tsa54/111.47 | gag/pol + 43.2 | 19.53 |
| tsa54/111.25 | gag/pol + 43.2 | 21.18 |
| tsa54/111.45 | gag/pol + 43.2 | 14.22 |
| tsa54/111.43 | gag/pol + 43.2 | 23.75 |
| tsa54/111.22 | gag/pol + 43.2 | 24.27 |

The four best clones were selected for long term stability studies with and without G418 selection. They were also assayed on PG4 cells for the production of RCR and are RCR negative.

Clone 111.4 is co-transfected with pIK6.1MCVamenvATGUTΔ and sv2his (Hartman and Mulligan, *Proc. Nat'l. Acad. Sci. (USA)* 85:8047–8051 (1988)) selected in histinol as described. Clones are picked and characterized for virus production by transient transfection as described above. Several high titer clones are characterized for stability and RCR as described.

Packaging lines can be created by replacing the amphotropic env gene in pIK6.1MCVamenvATGUTΔ with other retroviral envelopes, for example, ecotropic, xenotropic, polytropic, MLV, 10A1, Gibbon ape leukemia virus, feline leukemia virus C, Vesicular stomatitus virus (VSV) G protein, human T cell Leukemia (HTLV) I and II, and combinations thereof, using the methods described above.

All publications and patent applications cited in this specification are herein incorporated by reference in their entirety as if each individual publication or patent application were specifically and individually indicated to be incorporated by reference.

As will be apparent to those skilled in the art to which the invention pertains, the present invention may be embodied in forms other than those specifically disclosed above, for example to transfect and transduce other mammalian cell types, without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

What is claimed is:

1. A cell stably transfected with a retroviral packaging plasmid for the production of high titers of recombinant retrovirus in human cells comprising at least one retroviral helper DNA sequence derived from a replication-incompetent retroviral genome encoding in trans all virion proteins required for packaging a replication-incompetent retroviral vector and for producing virion proteins which package said replication-incompetent retroviral vector at high titer, without the production of replication-competent helper virus, said retroviral DNA sequence lacking the region encoding the native enhancer and/or promoter of the viral 5' long terminal repeat (LTR) of said virus and lacking both the psi function sequence responsible for the packaging helper genome and the 3'LTR, and encoding a foreign enchancer and/or promoter functional in a selected mammalian cell, and a SV40 polyadenylation site.

2. The cell of claim 1, wherein said cell is a cell.

3. The cell of claim 1 wherein said recombinant retrovirus is a leukemia retrovirus.

4. The cell of claim 3 wherein said leukemia retrovirus is selected from the group consisting of Moloney murine leukemia viruses (MMLV), Gibbon ape leukemia viruses (GALV), and human immunodeficiency viruses (HIV).

5. The cell of claim 4, wherein said foreign enhancer is the human cytomegalovirus (CMV) immediate early enhancer and said promoter is the native MMLV promoter.

6. The cell of claim 4, wherein said foreign enhancer and promoter is the human CMV immediate early enhancer and promoter.

7. The cell of claim 4, wherein said foreign enhancer and promoter is the Moloney Murine sarcoma virus (MMSV) enhancer and promoter.

8. The cells of claim 4, wherein said DNA construct comprises two retroviral helper DNA sequences.

9. The cell of claim 8, wherein a first helper sequence codes for ecotropic MMLV gag and pol proteins and a second helper sequence codes for env proteins, or combinations thereof, selected from virus of the group consisting of xenotropic murine leukemia virus, amphotropic murine leukemia virus, ecotropic murine leukemia virus, polytropic leukemia virus, 10A1 murine leukemia virus, GALV, HIV, Vesicular Stomatitis Virus (VSV), human T cell leukemia virus (HTLV) type I and HTLV type II.

10. The cell of claim 8 wherein a first helper sequence codes for HIV gag and pol proteins or GALV gag and pol proteins and a second helper sequence codes for env proteins, or combinations thereof, selected from virus of the group consisting of xenotropic murine leukemia virus, amphotropic murine leukemia virus, ecotropic murine leukemia virus, polytropic murine leukemia virus, 10A1 murine leukemia virus, GALV, HIV, Vesicular Stomatitis Virus (VSV), human T cell leukemia virus (HTLV) type I and HTLV type II.

11. The cell of claim 9, wherein said cell is a human cell.

12. A method for transducing mammalian target cells with foreign genes comprising:

A) stably transfecting a first population of mammalian cells that can produce virus with:
  (i) at least two retroviral packaging plasmids which are transfected sequentially comprising retroviral helper DNA sequences derived from a replication-incompetent retroviral genome encoding in trans all virion proteins required for packaging a replication-incompetent retroviral vector at high titer, without the production of replication-competent helper virus, said retroviral helper DNA sequence lacking the region encoding the native enhancer, the native promoter or both of the viral 5' long terminal repeat (LTR) of said virus and lacking both the psi function sequence responsible for packaging helper genome and the 3' LTR, and encoding a foreign enhancer, foreign promoter or both functional in a selected mammalian cell, and a SV40 polyadenylation site; and
  (ii) a retroviral vector encoding a foreign gen to produce replication-defective recombinant retroviral vectors carrying said foreign gene in said first population of mammalian cells;

B) separating said first population of mammalian cells from cell supernatant; and C) incubating said supernatant containing replication-defective recombinant retroviral vectors carrying said foreign gene with a second population of mammalian target cells to transduce said second population of target cells with said foreign gene, whereby target cells transduced with said foreign gene are obtained.

13. The method claim 12 wherein said first population of mammalian cells are human embryonic kidney cells.

14. The method of claim 12 wherein a first helper sequence codes for ecotropic MMLV gag and pol proteins and a second helper sequence codes for env proteins, or combinations thereof, selected from virus of the group consisting of xenotropic murine leukemia virus, amphotropic murine leukemia virus, ecotropic murine leukemia virus, polytropic murine leukemia virus, 10A1 murine leukemia virus, GALV, HIV, Vesicular Stomatitis Virus (VSV), human T cell leukemia virus (HTLV) type I and HTLV type II.

15. The method of 12 wherein a first helper sequence codes for HIV gag and pol proteins or GALV gag and pol proteins and a second helper sequence codes for env proteins, or combinations thereof, selected from virus of the group consisting of xenotropic murine leukemia virus, amphotropic murine leukemia virus, ecotropic murine leukemia virus, polytropic murine leukemia virus, 10A1 murine leukemia virus, GALV, HIV, Vesicular Stomatitis Virus (VSV) G, human T cell leukemia virus (HTLV) type I and HTLV type II.

16. The method of claim 13 wherein said human embryonic kidney cells are 293 cells.

17. The method of claim 16 wherein said 293 cells are tsa54 cells.

18. A cell line designated 90.74 ATCC No. CRL11654.

* * * * *

UNITED STATES PATENT AND TRADEMARK OFFICE
CERTIFICATE OF CORRECTION

PATENT NO. : 5,686,279
DATED : 11 November 1997
INVENTOR(S) : Mitchel H. FINER et al.

It is certified that error appears in the above-indentified patent and that said Letters Patent is hereby corrected as shown below:

Col. 11, line 11, delete "11647" and insert --1647--;

line 37, delete "it's" and insert --its--;

line 39, delete "of the".

Col. 19, line 19, delete "geF3" and insert --ge-F3--.

Col. 20, line 61, delete "Mack" and insert --Mock--.

Col. 23, line 44, delete "mi" and insert --ml--.

Col. 29, line 8, under "ATCC Accession No.", insert --CRL 11654--.

Col. 30, line 43, delete the second occurrence of "transient".

Col. 44, line 28, delete "gen" and insert --gene--; and line 42, after "method", insert --of--.

Signed and Sealed this

Eleventh Day of August 1998

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO.   : 5,686,279
DATED        : 11 November 1997
INVENTOR(S)  : Mitchell H. FINER et al.

It is certified that error(s) appears in the above-identified patent and that said Letters Patent is hereby corrected as shown below:

Claim 2, delete "is a cell" and insert --is a human cell--.

Signed and Sealed this

Twentieth Day of October, 1998

Attest:

BRUCE LEHMAN

*Attesting Officer*     *Commissioner of Patents and Trademarks*

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:1:

GGTCGACCTG GATCCGCCAT ACCACATTTG TAG 33

( 2 ) INFORMATION FOR SEQ ID NO:2:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:2:

GCCGCGGCTC TAGAGCCAGA CATGATAAGA TAC 33

( 2 ) INFORMATION FOR SEQ ID NO:3:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:3:

AAGCTTGTGC TAGCTATCCC GCCCCTAACT CCG 33

( 2 ) INFORMATION FOR SEQ ID NO:4:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

CGAAATCGGT CGACCGCAAA AGCCTAGGCC TCC 33

( 2 ) INFORMATION FOR SEQ ID NO:5:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

GTCTATAGCA TGCTCCCCTG CTCCGACCCG 30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GGTACCGAAT TCTCCTGCGG GGAGAAGCAG 30

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CGCCAAGCTT GGCCATTGCA TACGGT 26

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GAGGTCTAGA CGGTTCACTA AACGAGCTCT 30

( 2 ) INFORMATION FOR SEQ ID NO:9:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Gly Ser Thr Ser Gly Ser Gly Ser Ser Glu Gly Lys Gly
1             5                     10

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CGGAGATCTC GTGCGACCGC GAGAGCC 27

( 2 ) INFORMATION FOR SEQ ID NO:11:

( i ) SEQUENCE CHARACTERISTICS:
 ( A ) LENGTH: 38 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:11:

GGAATTCGCT AGCTTTCCAG GAGCGCAAAT GTTGTGTC   38

( 2 ) INFORMATION FOR SEQ ID NO:12:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:12:

CGGAGATCTC RCGCGACCCC GAGAGCC   27

( 2 ) INFORMATION FOR SEQ ID NO:13:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:13:

CGGGATCCAG AGCTGCAACT GGAG   24

( 2 ) INFORMATION FOR SEQ ID NO:14:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:14:

GAAGATCTGA CCTTGAAGAA GGTGAC   26

( 2 ) INFORMATION FOR SEQ ID NO:15:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:15:

TCTCCTCCAG TTGCAGCTCC GGAGACAGGG AGAGGC   36

( 2 ) INFORMATION FOR SEQ ID NO:16:

( i ) SEQUENCE CHARACTERISTICS:
  ( A ) LENGTH: 16 base pairs
  ( B ) TYPE: nucleic acid
  ( C ) STRANDEDNESS: single ( D ) TOPOLOGY: linear ( i i ) MOLECULE TYPE: DNA (genomic)

( x i ) SEQUENCE DESCRIPTION: SEQ ID NO:16:

TTGCAGCTCC GGAGAC 16

( 2 ) INFORMATION FOR SEQ ID NO:17:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CAGCACAATC AGGGCCATGT CCAGCTCCCC GTCCTG 36

( 2 ) INFORMATION FOR SEQ ID NO:18:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

AGGGCCATGT CCAGCT 16

( 2 ) INFORMATION FOR SEQ ID NO:19:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

CGGAATTCGG TACCTCCTGT GCAAGAAC 28

( 2 ) INFORMATION FOR SEQ ID NO:20:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

CGGAATTCGC CTCCACCAAG GGCCCA 26

( 2 ) INFORMATION FOR SEQ ID NO:21:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

```
CGGAATTCAC GCGTCCCAGT CAGGACACAG C                                               31
```

( 2 ) INFORMATION FOR SEQ ID NO:22:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
GAGAGAGATC TGCTAGCGGT CAGGCTGGAA CTGAG                                            35
```

( 2 ) INFORMATION FOR SEQ ID NO:23:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
GCATGTGTGA GTTTGTCTG AGGAGACGGT GACCAG                                            36
```

( 2 ) INFORMATION FOR SEQ ID NO:24:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
GTTTTGTCTG AGGAGA                                                                 16
```

( 2 ) INFORMATION FOR SEQ ID NO:25:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

```
GTGACAGTCG ACCCCTTGAA GTCCACTTTG GT                                               32
```

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

```
CCACCCCTCA CTCTGCTTCT C                                                           21
```

( 2 ) INFORMATION FOR SEQ ID NO:27:

(i) SEQUENCE CHARACTERISTICS:
    (A) LENGTH: 43 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:27:

TCGACCAGCG GCAGCGGCAA GAGCAGCGAG GGTAAGGGTA CCA          43

(2) INFORMATION FOR SEQ ID NO:28:

(i) SEQUENCE CHARACTERISTICS:
    (A) LENGTH: 43 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:28:

GATCTGGTAC CCTTACCCTC GCTGCTCTTG CCGCTGCCGC TGG          43

(2) INFORMATION FOR SEQ ID NO:29:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:29:

CTCCTGTAGT AGCACCTGAC CCTTACCCTC GCTGCT                  36

(2) INFORMATION FOR SEQ ID NO:30:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:30:

AGCACCTGAC CCTTAC                                        16

(2) INFORMATION FOR SEQ ID NO:31:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:31:

CTGATCTTAC TCTTTGGACC                                    20

(2) INFORMATION FOR SEQ ID NO:32:

(i) SEQUENCE CHARACTERISTICS:
    (A) LENGTH: 32 base pairs
    (B) TYPE: nucleic acid
    (C) STRANDEDNESS: single

```
(  D  ) TOPOLOGY: linear ( i i ) MOLECULE TYPE: DNA (genomic)

( x i ) SEQUENCE DESCRIPTION: SEQ ID NO:32:

GAATTCGCTA   GCCTATGGCT   CGTACTCTAT   AG                                                       3 2
```